United States Patent
Luo et al.

(10) Patent No.: US 11,970,519 B2
(45) Date of Patent: Apr. 30, 2024

(54) GENE THERAPY VECTOR FOR TREATING RETINITIS PIGMENTOSA DISEASE

(71) Applicant: Shanghai Innostellar Biotherapeutics Co., Ltd., Shanghai (CN)

(72) Inventors: Xueting Luo, Shanghai (CN); Xiaodong Sun, Shanghai (CN)

(73) Assignee: Shanghai Innostellar Biotherapeutics Co., Ltd., Shanghai (CN)

( * ) Notice: Subject to any disclaimer, the term of this patent is extended or adjusted under 35 U.S.C. 154(b) by 106 days.

(21) Appl. No.: 17/244,574

(22) Filed: Apr. 29, 2021

(65) Prior Publication Data

US 2021/0347834 A1   Nov. 11, 2021

Related U.S. Application Data

(63) Continuation of application No. PCT/CN2019/114446, filed on Oct. 30, 2019.

(51) Int. Cl.
  *C07K 14/47*   (2006.01)
  *A61K 48/00*   (2006.01)
  *A61P 27/02*   (2006.01)

(52) U.S. Cl.
  CPC ............ *C07K 14/47* (2013.01); *A61K 48/005* (2013.01); *A61P 27/02* (2018.01)

(58) Field of Classification Search
  None
  See application file for complete search history.

(56) References Cited

FOREIGN PATENT DOCUMENTS

| JP | 2017-121241 A | 7/2017 |
| WO | WO 2016/141078 A1 | 9/2016 |

OTHER PUBLICATIONS

Extended European Search Report for Application No. 19877780.7, dated Jun. 20, 2022.
International Search Report and Written Opinion for Application No. PCT/CN2019/114446, dated Feb. 1, 2020.
International Preliminary Report on Patentability for Application No. PCT/CN2019/114446, dated May 14, 2021.
Fahim et al., Nonsyndromic Retinitis Pigmentosa Overview. GeneReviews. Aug. 4, 2000; Last updated: Jan. 19, 2017. 26 pages.
Fischer et al., Codon-Optimized RPGR Improves Stability and Efficacy of AAV8 Gene Therapy in Two Mouse Models of X-Linked Retinitis Pigmentosa. Mol Ther. Aug. 2, 2017;25(8):1854-1865. doi: 10.1016/j.ymthe.2017.05.005. Epub May 24, 2017.
Genbank Submission; NCBI, Accession No. LX405239, Version LX405239.1; JP2017121241-A/59280: Modified Polynucleotides For The Production Of Proteins Associated With Human Disease. Whoriskey et al.; Oct. 28, 2017.
Genbank Submission; NCBI, Accession No. NM_001145850, Version 001145850.1; *Homo sapiens* prominin 1 (PROM1), transcript variant 6, mRNA. Sep. 2, 2018.
Genbank Submission; NCBI, Accession No. NP_001139322, Version NP_001139322.1; prominin-1 isoform 6 precursor [*Homo sapiens*]. Lee et al.; Oct. 14, 2018.
Permanyer et al., Autosomal recessive retinitis pigmentosa with early macular affectation caused by premature truncation in PROM1. Invest Ophthalmol Vis Sci. May 2010;51(5):2656-63. doi: 10.1167/iovs.09-4857. Epub Dec. 30, 2009.
Sengillo et al., Correction of Monogenic and Common Retinal Disorders with Gene Therapy. Genes (Basel). Jan. 27, 2017;8(2):53. doi: 10.3390/genes8020053.

*Primary Examiner* — Nancy J Leith
*Assistant Examiner* — Khaleda B Hasan
(74) *Attorney, Agent, or Firm* — Wolf, Greenfield & Sacks, P.C.

(57) ABSTRACT

Provided, in an aspect, is a gene therapy vector, such as for treating retinitis pigmentosa. In an embodiment, a target specific optimization design is performed on a PROM1 gene coding sequence to obtain a nucleotide sequence particularly suitable for efficiently expressing a PROM1 protein in a mammalian cell, and a recombinant AAV virus for expressing a normal human PROM1 protein is constructed. Compared with a coding sequence which is not optimized, the expression level of the optimized PROM1 coding sequence (SEQ ID NO.:1) is increased more than three times. The sequence is particularly suitable for expression in a mammalian cell.

15 Claims, 2 Drawing Sheets

Specification includes a Sequence Listing.

SEQUENCE LISTING

<160> NUMBER OF SEQ ID NOS: 4

<210> SEQ ID NO 1
<211> LENGTH: 2505
<212> TYPE: DNA
<213> ORGANISM: Artificial Sequence
<220> FEATURE:
<223> OTHER INFORMATION: Synthetic

<400> SEQUENCE: 1

```
atggccctgg tgctggggag cctgctgctg ctggggctgt gcggaaactc cttctccggg      60
ggccagccct ccagcaccga cgctcctaag gcctggaact acgagctgcc cgccaccaac     120
tacgaaaccc aagactccca caaagccggc cccatcggca tcctgttcga actcgtgcat     180
attttcctct acgtggttca acccagagat tttcccgagg acaccctgag aaagttcctg     240
cagaaggcct atgagagcaa gattgactac gacaagcccg aaaccgtgat cctgggcctg     300
aagatcgtgt attatgaggc cggaattatc ctctgttgcg tgctgggcct gctgtttatc     360
atcctgatgc cactggtggg ctacttcttt tgcatgtgca gatgttgcaa caagtgtggc     420
ggcgagatgc accagcgtca gaaggagaac gggcctttcc tccggaaatg ctttgccatc     480
tccctgctgg tgatttgtat cattatcagc atcgggatct tctacggatt cgtggctaac     540
catcaggtca gaacccgcat caagcgcagt agaaagctgg ccgactccaa cttcaaggac     600
ctgcggaccc tgctgaacga gacccccgag cagatcaagt acattctggc ccaatacaac     660
accaccaagg acaaagcctt cacagacctg aactccatca cagcgtgct cggcggaggc     720
```

```
atactggacc ggctgagacc caacataata cccgtgctgg acgaaatcaa aagcatggcc      780
accgccataa aggagaccaa agaagccctc gaaaacatga actccaccct gaaaagcctc      840
caccaacaaa gcacccagct cagcagctcc ctgaccagcg tgaaaacaag cctgagaagc      900
agcctgaacg acccctgtg cctcgtccac cccagcagcg agacctgcaa cagcatcaga       960
ctcagcctca gccaactcaa cagcaacccc gaactcagac aactccccc cgtggacgcc      1020 gaactggaca cgtcaacaa cgtgctcaga acagacctgg acggcctcgt gcagcagggc      1080
taccaaagcc tcaacgacat ccccgacaga gtgcagagac aaaccaccac cgtggtggcc      1140
ggaattaaga gagtcctgaa tagcatcggc agcgacattg acaacgtgac acaaagactc      1200
cccatccaag acatactgag cgccttcagt gtgtacgtca acaacaccga gagttacata      1260 cacagaaaacc tgcccacccct ggaggagtac gacagctact ggtggctggg cggactcgtc      1320
atctgcagcc tcctgacccct gatcgtgatt ttctattacc tgggcctgct ctgcggcgtc      1380
tgcggctacg accgcacgc cacccacc acaagggget gcgtgtctaa taccggcggc       1440
gtgttcctca tggtgggcgt cggactgtcc ttcctgttct gttggatcct gatgattatt      1500
gttgtgctga ccttcgtttt cggcgccaac gtggagaagc tgatctgcga gccctacacc      1560
tccaaagagc tgttcagagt gctggacacc ccctatctgc tgaacgaaga ctgggagtat      1620
tacctgagcg gcaagctgtt taataagagt aagatgaaac tgaccttcga gcaggtgtat      1680
agcgactgca agaaaaaccg cggaacctac ggcaccctgc acctgcagaa cagcttcaac      1740
atttcagagc acctcaacat caacgagcac accggctcca tcagcagcga actggagagc      1800
ctgaaggtga acctgaacat cttcctgctg ggcgccgcag gcagaaaaaa cctgcaggac      1860
ttcgccgcct gcggcatcga cagaatgaac tacgacagct acctggccca gaccggcaag      1920
agccccgccg gcgtgaacct gctgagcttc gcctacgacc tggaggccaa ggccaacagc      1980
ctgccccccg gcaacctgag aaacagcctg aagagagacg cccagaccat caagaccatc      2040
caccagcaga gagtgctgcc catcgagcag agcctgagca ccctgtacca gagcgtgaag      2100
atcctgcaga gaaccggcaa cggcctgctg agagagtga ccagaatcct ggccagcctg      2160
gacttcgccc agaacttcat caccaacaac accagcagcg tgatcatcga ggagaccaag      2220
aagtacggca gaaccatcat cggctacttc gagcactacc tgcagtggat cgagttcagc      2280
atcagcgaga aggtggccag ctgcaagccc gtggccaccg ccctggacac cgccgtggac      2340
gtgttcctgt gcagctacat catcgacccc ctgaacctgt tctggttcgg catcggcaag      2400
gccaccgtgt cctgctgcc cgccctgatc ttcgccgtga agctggccaa gtactacaga      2460
agaatggaca gcgaggacgt gtacgacgac cccagccagc actga                     2505

<210> SEQ ID NO 2
<211> LENGTH: 2505
<212> TYPE: DNA
<213> ORGANISM: Homo sapiens

<400> SEQUENCE: 2
atggccctcg tactcggctc cctgttgctg ctggggctgt gcgggaactc cttttcagga       60
gggcagcctt catccacaga tgctcctaag gcttggaatt atgaattgcc tgcaacaaat      120
tatgagaccc aagactccca taaagctgga cccattggca ttctctttga actagtgcat      180
atctttctct atgtggtaca gccgcgtgat ttcccagaag atactttgag aaaattctta      240
cagaaggcat atgaatccaa aattgattat gacaagccag aaactgtaat cttaggtcta      300
aagattgtct actatgaagc agggattatt ctatgctgtg tcctggggct gctgtttatt      360
```

```
attctgatgc ctctggtggg gtatttcttt tgtatgtgtc gttgctgtaa caaatgtggt    420
ggagaaatgc accagcgaca gaaggaaaat gggcccttcc tgaggaaatg ctttgcaatc    480
tccctgttgg tgatttgtat aataataagc attggcatct tctatggttt tgtggcaaat    540
caccaggtaa gaacccggat caaaaggagt cggaaactgg cagatagcaa tttcaaggac    600
ttgcgaactc tcttgaatga aactccagag caaatcaaat atatattggc ccagtacaac    660
actaccaagg acaaggcgtt cacagatctg aacagtatca attcagtgct aggaggcgga    720
attcttgacc gactgagacc caacatcatc cctgttcttg atgagattaa gtccatggca    780
acagcgatca aggagaccaa agaggcgttg gagaacatga acagcacctt gaagagcttg    840
caccaacaaa gtacacagct tagcagcagt ctgaccagcg tgaaaactag cctgcggtca    900
tctctcaatg accctctgtg cttggtgcat ccatcaagtg aaacctgcaa cagcatcaga    960
ttgtctctaa gccagctgaa tagcaaccct gaactgaggc agcttccacc cgtggatgca   1020
gaacttgaca cgttaataaa cgttcttagg acagatttgg atggcctggt ccaacagggc   1080
tatcaatccc ttaatgatat acctgacaga gtacaacgcc aaaccacgac tgtcgtagca   1140
ggtatcaaaa gggtcttgaa ttccattggt tcagatatcg acaatgtaac tcagcgtctt   1200
cctattcagg atatactctc agcattctct gtttatgtta ataacactga aagttacatc   1260
cacagaaatt tacctacatt ggaagagtat gattcatact ggtggctggg tggcctggtc   1320
atctgctctc tgctgaccct catcgtgatt ttttactacc tgggcttact gtgtggcgtg   1380
tgcggctatg acaggcatgc caccccgacc acccgaggct gtgtctccaa caccggaggc   1440
gtcttcctca tggttggagt tggattaagt ttcctctttt gctggatatt gatgatcatt   1500
gtggttctta cctttgtctt tggtgcaaat gtggaaaaac tgatctgtga accttacacg   1560
agcaaggaat tattccgggt tttggataca ccctacttac taaatgaaga ctgggaatac   1620
tatctctctg ggaagctatt taataaatca aaaatgaagc tcacttttga acaagtttac   1680
agtgactgca aaaaaaatag aggcacttac ggcactcttc acctgcagaa cagcttcaat   1740
atcagtgaac atctcaacat taatgagcat actggaagca taagcagtga attggaaagt   1800
ctgaaggtaa atcttaatat cttttctgttg ggtgcagcag gaagaaaaaa ccttcaggat   1860
tttgctgctt gtggaataga cagaatgaat tatgacagct acttggctca gactggtaaa   1920
tcccccgcag gagtgaatct tttatcattt gcatatgatc tagaagcaaa agcaaacagt   1980
ttgcccccag gaaatttgag gaactccctg aaaagagatg cacaaactat taaaacaatt   2040
caccagcaac gagtccttcc tatagaacaa tcactgagca ctctatacca aagcgtcaag   2100
atacttcaac gcacagggaa tggattgttg gagagagtaa ctaggattct agcttctctg   2160
gattttgctc agaacttcat cacaaacaat acttcctctg ttattattga ggaaactaag   2220
aagtatggga gaacaataat aggatatttt gaacattatc tgcagtggat cgagttctct   2280
atcagtgaga agtggcatc gtgcaaacct gtggccaccg ctctagatac tgctgttgat   2340
gtctttctgt gtagctacat tatcgacccc ttgaatttgt tttggtttgg cataggaaaa   2400
gctactgtat ttttacttcc ggctctaatt tttgcggtaa aactggctaa gtactatcgt   2460
cgaatggatt cggaggacgt gtacgatgac ccatcacaac attga                   2505

<210> SEQ ID NO 3
<211> LENGTH: 834
<212> TYPE: PRT
<213> ORGANISM: Homo sapiens
```

<400> SEQUENCE: 3

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
            35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
        210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
            245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
        290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
            325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
        370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
            405                 410                 415
```

-continued

```
Glu Ser Tyr Ile His Arg Asn Leu Pro Thr Leu Glu Tyr Asp Ser
                420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
        450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Arg Val Leu Pro Ile
        675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Pro Ser
            820                 825                 830
```

Gln His

<210> SEQ ID NO 4
<211> LENGTH: 6495
<212> TYPE: DNA
<213> ORGANISM: Artificial Sequence
<220> FEATURE:
<223> OTHER INFORMATION: Synthetic

<400> SEQUENCE: 4

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggggttcc | tgcggccgcg | tcgacattga | ttattgacta | gttattaata | 180 |
| gtaatcaatt | acgggtcat | tagttcatag | cccatatatg | gagttccgcg | ttacataact | 240 |
| tacggtaaat | ggcccgcctg | gctgaccgcc | caacgacccc | cgcccattga | cgtcaataat | 300 |
| gacgtatgtt | cccatagtaa | cgccaatagg | gactttccat | tgacgtcaat | gggtggacta | 360 |
| tttacggtaa | actgcccact | tggcagtaca | tcaagtgtat | catatgccaa | gtacgccccc | 420 |
| tattgacgtc | aatgacggta | aatggcccgc | ctggcattat | gcccagtaca | tgaccttatg | 480 |
| ggactttcct | acttggcagt | acatctacgt | attagtcatc | gctattacca | tgggtcgagg | 540 |
| tgagccccac | gttctgcttc | actctcccca | tctcccccc | ctccccaccc | ccaattttgt | 600 |
| atttatttat | tttttaatta | ttttgtgcag | cgatgggggc | gggggggggg | ggggcgcgcg | 660 |
| ccaggcgggg | cggggcgggg | cgaggggcgg | ggcggggcga | ggcggagagg | tgcggcggca | 720 |
| gccaatcaga | gcggcgcgct | ccgaaagttt | ccttttatgg | cgaggcggcg | gcggcggcgg | 780 |
| ccctataaaa | agcgaagcgc | gcggcgggcg | tctagaggat | ccggtactag | aggaactgaa | 840 |
| aaaccagaaa | gttaactggt | aagtttagtc | tttttgtctt | ttatttcagg | tcccggatcc | 900 |
| ggtggtggtg | caaatcaaag | aactgctcct | cagtggatgt | tgcctttact | tctaggcctg | 960 |
| tacgaagtg | ttacttctgc | tctaaaagct | gcggaattgt | accgcggga | attccaccat | 1020 |
| ggccctggtg | ctggggagcc | tgctgctgct | ggggctgtgc | ggaaactcct | tctccggggg | 1080 |
| ccagcccctcc | agcaccgacg | ctcctaaggc | ctggaactac | gagctgcccg | ccaccaacta | 1140 |
| cgaaacccaa | gactcccaca | aagccggccc | catcggcatc | ctgttcgaac | tcgtgcatat | 1200 |
| tttcctctac | gtggttcaac | ccagagattt | tcccgaggac | accctgagaa | agttcctgca | 1260 |
| gaaggcctat | gagagcaaga | ttgactacga | caagcccgaa | accgtgatcc | tgggcctgaa | 1320 |
| gatcgtgtat | tatgaggccg | gaattatcct | ctgttgcgtg | ctgggcctgc | tgtttatcat | 1380 |
| cctgatgcca | ctggtgggct | acttcttttg | catgtgcaga | tgttgcaaca | agtgtggcgg | 1440 |
| cgagatgcac | cagcgtcaga | aggagaacgg | gcctttcctc | cggaaatgct | ttgccatctc | 1500 |
| cctgctggtg | atttgtatca | ttatcagcat | cgggatcttc | tacggattcg | tggctaacca | 1560 |
| tcaggtcaga | acccgcatca | agcgcagtag | aaagctggcc | gactccaact | tcaaggacct | 1620 |
| gcggacccctg | ctgaacgaga | ccccccagca | gatcaagtac | attctggccc | aatacaacac | 1680 |
| caccaaggac | aaagccttca | cagacctgaa | ctccatcaac | agcgtgctcg | gcggaggcat | 1740 |
| actgaccgg | ctgagaccca | acataatacc | cgtgctggac | gaaatcaaaa | gcatggccac | 1800 |
| cgccataaag | gagaccaaag | aagccctcga | aacatgaac | tccaccctga | aaagcctcca | 1860 |
| ccaacaaagc | acccagctca | gcagctccct | gaccagcgtg | aaaacaagcc | tgaagcag | 1920 |
| cctgaacgac | ccctgtgcc | tcgtccaccc | cagcagcgag | acctgcaaca | gcatcagact | 1980 |
| cagcctcagc | caactcaaca | gcaaccccga | actcagacaa | ctccccccg | tggacgccga | 2040 |

-continued

```
actggacaac gtcaacaacg tgctcagaac agacctggac ggcctcgtgc agcagggcta      2100
ccaaagcctc aacgacatcc ccgacagagt gcagagacaa accaccaccg tggtggccgg      2160
aattaagaga gtcctgaata gcatcggcag cgacattgac aacgtgacac aaagactccc      2220
catccaagac atactgagcg ccttcagtgt gtacgtcaac aacaccgaga gttacataca      2280
cagaaacctg cccaccctgg aggagtacga cagctactgg tggctgggcg actcgtcat      2340 ctgcagcctc ctgaccctga tcgtgatttt ctattacctg gcctgctct gcggcgtctg      2400 cggctacgac cgacacgcca cacccaccac aaggggctgc gtgtctaata ccggcggcgt      2460
gttcctcatg gtgggcgtcg gactgtcctt cctgttctgt tggatcctga tgattattgt      2520
tgtgctgacc ttcgttttcg gcgccaacgt ggagaagctg atctgcgagc cctacacctc      2580
caaagagctg ttcagagtgc tggacacccc ctatctgctg aacgaagact gggagtatta      2640
cctgagcggc aagctgtttta ataagagtaa gatgaaactg accttcgagc aggtgtatag      2700
cgactgcaag aaaaaccgcg gaacctacgg cacccctgcac ctgcagaaca gcttcaacat      2760
ttcagagcac ctcaacatca acgagcacac cggctccatc agcagcgaac tggagagcct      2820
gaaggtgaac ctgaacatct tcctgctggg cgccgcaggc agaaaaaacc tgcaggactt      2880
cgccgcctgc ggcatcgaca gaatgaacta cgacagctac ctggcccaga ccggcaagag      2940
ccccgccggc gtgaacctgc tgagcttcgc ctacgacctg gaggccaagg ccaacagcct      3000
gccccccggc aacctgagaa acagcctgaa gagagacgcc cagaccatca gaccatcca      3060 ccagcagaga gtgctgccca tcgagcagag cctgagcacc ctgtaccaga gcgtgaagat      3120
cctgcagaga accggcaacg gcctgctgga gagagtgacc agaatcctgg ccagcctgga      3180
cttcgcccag aacttcatca ccaacaacac cagcagcgtg atcatcgagg agaccaagaa      3240
gtacggcaga accatcatcg gctacttcga gcactacctg cagtggatcg agttcagcat      3300
cagcgagaag gtggccagct gcaagcccgt ggccaccgcc ctggacaccg ccgtggacgt      3360
gttcctgtgc agctacatca tcgaccccct gaacctgttc tggttcggca tcggcaaggc      3420
caccgtgttc ctgctgcccg ccctgatctt cgccgtgaag ctggccaagt actacagaag      3480
aatggacagc gaggacgtgt acgacgaccc cagccagcac tgactcgagc gcggatccag      3540
acatgataag atacattgat gagtttggac aaaccacaac tagaatgcag tgaaaaaaat      3600
gctttatttg tgaaatttgt gatgctattg ctttatttgt aaccattata agctgcaata      3660
aacaagttaa caacaacaat tgcattcatt ttatgtttca ggttcagggg gaggtgtggg      3720 aggttttttta gtcgactggg gagagatctg cggccgcagg aaccccctagt gatggagttg      3780 gccactccct ctctgcgcgc tcgctcgctc actgaggccg ggcgaccaaa ggtcgcccga      3840 cgccgggct tgcccgggc ggcctcagtg agcgagcgag cgcgcagctg cctgcagggg      3900
cgcctgatgc ggtatttttct ccttacgcat ctgtgcggta tttcacaccg catacgtcaa      3960
agcaaccata gtacgcgccc tgtagcgcg cattaagcgc ggcgggtgtg tggttacgc      4020 gcagcgtgac cgctacactt gccagcgccc tagcgcccgc tcctttcgct ttcttccctt      4080
cctttctcgc cacgttcgcc ggctttcccc gtcaagctct aaatcggggg ctccctttag      4140
ggttccgatt tagtgcttta cggcacctcg accccaaaaa acttgatttg ggtgatggtt      4200
cacgtagtgg gccatcgccc tgatagacgg ttttttcgccc tttgacgttg gagtccacgt      4260
tctttaatag tggactcttg ttccaaactg gaacaacact caaccctatc tcgggctatt      4320
cttttgattt ataagggatt ttgccgattt cggcctattg gttaaaaaat gagctgattt      4380
```

| | |
|---|---|
| aacaaaaatt taacgcgaat tttaacaaaa tattaacgtt tacaatttta tggtgcactc | 4440 |
| tcagtacaat ctgctctgat gccgcatagt taagccagcc ccgacacccg ccaacacccg | 4500 |
| ctgacgcgcc ctgacgggct tgtctgctcc cggcatccgc ttacagacaa gctgtgaccg | 4560 |
| tctccgggag ctgcatgtgt cagaggtttt caccgtcatc accgaaacgc gcgagacgaa | 4620 |
| agggcctcgt gatacgccta ttttataggt taatgtcatg ataataatg gtttcttaga | 4680 |
| cgtcaggtgg cacttttcgg ggaaatgtgc gcggaacccc tatttgttta tttttctaaa | 4740 |
| tacattcaaa tatgtatccg ctcatgagac aataaccctg ataaatgctt caataatatt | 4800 |
| gaaaaaggaa gagtatgagt attcaacatt tccgtgtcgc ccttattccc ttttttgcgg | 4860 |
| cattttgcct tcctgttttt gctcacccag aaacgctggt gaaagtaaaa gatgctgaag | 4920 |
| atcagttggg tgcacgagtg ggttacatcg aactggatct caacagcggt aagatccttg | 4980 |
| agagttttcg ccccgaagaa cgttttccaa tgatgagcac ttttaaagtt ctgctatgtg | 5040 |
| gcgcggtatt atcccgtatt gacgccgggc aagagcaact cggtcgccgc atacactatt | 5100 |
| ctcagaatga cttggttgag tactcaccag tcacagaaaa gcatcttacg gatggcatga | 5160 |
| cagtaagaga attatgcagt gctgccataa ccatgagtga taacactgcg gccaacttac | 5220 |
| ttctgacaac gatcggagga ccgaaggagc taaccgcttt tttgcacaac atgggggatc | 5280 |
| atgtaactcg ccttgatcgt tgggaaccgg agctgaatga agccatacca aacgacgagc | 5340 |
| gtgacaccac gatgcctgta gcaatggcaa caacgttgcg caaactatta actggcgaac | 5400 |
| tacttactct agcttcccgg caacaattaa tagactggat ggaggcggat aaagttgcag | 5460 |
| gaccacttct gcgctcggcc cttccggctg gctggtttat tgctgataaa tctggagccg | 5520 |
| gtgagcgtgg gtctcgcggt atcattgcag cactggggcc agatggtaag ccctcccgta | 5580 |
| tcgtagttat ctacacgacg gggagtcagg caactatgga tgaacgaaat agacagatcg | 5640 |
| ctgagatagg tgcctcactg attaagcatt ggtaactgtc agaccaagtt tactcatata | 5700 |
| tactttagat tgatttaaaa cttcattttt aatttaaaag gatctaggtg aagatccttt | 5760 |
| ttgataatct catgaccaaa atcccttaac gtgagttttc gttccactga gcgtcagacc | 5820 |
| ccgtagaaaa gatcaaagga tcttcttgag atcctttttt tctgcgcgta atctgctgct | 5880 |
| tgcaaacaaa aaaaccaccg ctaccagcgg tggtttgttt gccggatcaa gagctaccaa | 5940 |
| ctcttttttcc gaaggtaact ggcttcagca gagcgcagat accaaatact gtccttctag | 6000 |
| tgtagccgta gttaggccac cacttcaaga actctgtagc accgcctaca tacctcgctc | 6060 |
| tgctaatcct gttaccagtg gctgctgcca gtggcgataa gtcgtgtctt accgggttgg | 6120 |
| actcaagacg atagttaccg gataaggcgc agcggtcggg ctgaacgggg ggttcgtgca | 6180 |
| cacagcccag cttggagcga acgacctaca ccgaactgag atacctacag cgtgagctat | 6240 |
| gagaaagcgc cacgcttccc gaagggagaa aggcggacag gtatccggta agcggcaggg | 6300 |
| tcggaacagg agagcgcacg agggagcttc caggggggaaa cgcctggtat ctttatagtc | 6360 |
| ctgtcgggtt tcgccacctc tgacttgagc gtcgattttt gtgatgctcg tcagggggc | 6420 |
| ggagcctatg gaaaaacgcc agcaacgcgg cctttttacg gttcctggcc ttttgctggc | 6480 |
| cttttgctca catgt | 6495 |

GENE THERAPY VECTOR FOR TREATING RETINITIS PIGMENTOSA DISEASE

RELATED APPLICATIONS

This application is a continuation of International Application No. PCT/CN2019/114446, filed Oct. 30, 2019, which claims the benefit under 35 U.S.C. § 119(a)-(d) or 35 U.S.C. § 365(b) to Chinese Application No. 201811280540.4, filed Oct. 30, 2018, the contents of each of which are incorporated herein by reference in their entireties.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. The ASCII file, created on Jul. 17, 2023, is named X002570027US00-SEQ-KVC, and is 22,883 bytes in size.

TECHNICAL FIELD

The present invention relates to the technical field of genetic engineering, in particular to gene therapy vector for treating retinitis pigmentosa disease.

BACKGROUND ART

Retinitis pigmentosa (RP) is a group of diseases characterized by hereditary and progressive loss of photoreceptor cells and eventually leading to retinal degeneration and atrophy, accompanied by retinal pigment epithelium (RPE) cells dystrophy and degenerative change. The literature reports that the prevalence rate of RP is about 1/4,000 worldwide, and more than 1.5 million patients suffer from progressive visual impairment. Lesions usually start from the equatorial part of retina and advance to macula and fovea. Its main manifestations are night blindness, progressive peripheral visual field decline, and vision decline caused by photoreceptor cell death, etc. In fundus oculi, the retinal blood vessels become thin, showing white-line like stenosis, and the macular area has atrophic-like changes. Osteocyte-like pigmentation started at the equator and gradually developed to the posterior pole. Electroretinogram showed that the amplitude of a and b waves decreased and the incubation period prolonged. Patients may also be accompanied by hearing loss, metabolic abnormalities, neuropathy, liver or kidney diseases and other systemic manifestations.

With the continuous progress of science and technology, people have a certain understanding of the disease characteristics of RP. The death of photoreceptor cells is the main pathological feature of RP, which will eventually lead to blindness of patients. Previous studies have found that the phagocytic function of RPE cells to the shed membrane disc of the outer segment of the photoreceptor cell decreases, and the membrane disc that is not phagocytized accumulates in the outer layer of retina, destroying the original retinal structure, leading to degeneration and death of photoreceptor cells, thus triggering RP. The pathogenic mechanism is mainly the dysfunction or deletion of corresponding normal proteins caused by gene mutation. Due to its significant genetic heterogeneity and complex pathogenic mechanism, there is no clear treatment for this disease at present.

There are many inheritance modes of RP, including autosomal dominant inheritance, autosomal recessive inheritance and X chromosome linkage inheritance. Up to now, 64 genes have been found to be related to the occurrence of RP (sph.uth.edu/retnet/sum-dis.htm), including PROM1. With the successful construction of human gene map, the rapid development of molecular biology technology and the successful application of virus vector, some progress has been made in gene therapy of RP. Many experimental studies have done a lot of foreshadowing and preliminary work for the clinical application of gene therapy for RP. Because adeno-associated virus (AAV) is smaller than other viral vectors, non-pathogenic, and can transfect dividing and non-dividing cells, gene therapy based on AAV vector for eye, especially hereditary retinal degeneration, has attracted wide attention.

Therefore, there is an urgent need to develop gene therapy methods and therapeutic drugs that can effectively treat hereditary retinal degeneration.

SUMMARY OF THE INVENTION

The object of the present invention is to provide a gene therapy drug that can effectively treat hereditary retinal degeneration.

Another object of the present invention is to provide a recombinant AAV virus expressing normal human PROM1 protein.

In a first aspect of the present invention, it provides a nucleotide sequence, the nucleotide sequence encodes a PROM1 protein and is selected from the group consisting of:

(a) the nucleotide sequence is shown in SEQ ID NO: 1; and (b) the nucleotide sequence is of ≥95%, preferably ≥98%, more preferably ≥99% homologous to the sequence as shown in SEQ ID NO: 1;

(c) a nucleotide sequence complementary to the nucleotide sequence of (a) or (b).

In another preferred embodiment, the nucleotide sequence comprises a DNA sequence, a cDNA sequence, or a mRNA sequence.

In another preferred embodiment, the nucleotide sequence comprises a single-stranded sequence and a double-stranded sequence.

In another preferred embodiment, the nucleotide sequence comprises a nucleotide sequence completely complementary to SEQ ID NO: 1.

In a second aspect of the present invention, it provides an expression cassette comprising the nucleotide sequence according to the first aspect of the present invention.

In another preferred embodiment, the expression cassette has a structure of Formula I from the 5'-3' end:

$$Z1\text{-}Z2\text{-}Z3\text{-}Z4\text{-}Z5 \qquad (I)$$

wherein, each "-" is independently a bond or nucleotide linker sequence;

Z1 is none or an enhancer;

Z2 is a promoter;

Z3 is none or an intron;

Z4 is the nucleotide sequence according to the first aspect of the present invention; and Z5 is none or a polyA.

In another preferred embodiment, the enhancer is a CMV enhancer.

In another preferred embodiment, the promoter is a chicken β actin promoter (CBA promote).

In another preferred embodiment, the intron is a sv40 intron.

In another preferred embodiment, the polyA is a sv40 polyA.

In another preferred embodiment, the length of each nucleotide linker sequence is from 0 to 30 nt, preferably from 1 to 15 nt.

In a third aspect of the present invention, it provides a vector comprising a nucleotide sequence according to the first aspect of the present invention or the expression cassette according to the second aspect of the present invention.

In another preferred embodiment, the vector comprises one or more promoters operably linked to the nucleic acid sequence, enhancer, intron, transcription termination signal, polyadenylation sequence, origin of replication, selective marker, nucleic acid restriction site, and/or homologous recombination site.

In another preferred embodiment, the vector comprises a plasmid or a viral vector.

In another preferred embodiment, the vector comprises a DNA virus or a retroviral vector.

In another preferred embodiment, the vector is selected from the group consisting of: lentiviral vectors, adenoviral vectors, adeno-associated viral vectors (AAV), and a combination thereof. Preferably, the vector is an AAV vector.

In another preferred embodiment, the vector is an AAV vector containing or inserted with the nucleotide sequence according to the first aspect of the invention.

In another preferred embodiment, the vector is used to express human PROM1 protein.

In a fourth aspect of the present invention, it provides an adeno-associated viral vector comprising the nucleotide sequence according to the first aspect of the present invention or the expression cassette according to the second aspect of the present invention.

In another preferred embodiment, the serotype of the adeno-associated virus is selected from the group consisting of: AAV1, AAV2, AAV3, AAV4, AAV5, AAV6, AAV7, AAV8, AAV9, rh10, and a combination thereof.

In another preferred embodiment, the adeno-associated virus vector is used to treat eye diseases and/or restore the subject's vision or photosensitivity.

In another preferred embodiment, the sequence of the adeno-associated virus vector is shown in SEQ ID NO: 4.

Wherein positions 1-141 are left ITR sequence;
positions 153-532 are CMV enhancer;
positions 535-810 are chicken β actin promoter (CBA promoter);
positions 813-1006 are SV40 intron;
positions 1019-3523 are the optimized human PROM1 coding sequence;
positions 3530-3757 are SV40 PolyA;
positions 3758-3898 are right ITR sequence.

In a fifth aspect of the present invention, it provides a host cell comprising the vector according to the third aspect of the present invention or the adeno-associated virus vector according to the fourth aspect of the present invention, or having an exogenous nucleotide sequence according to the first aspect of the present invention or expression cassette according to the second aspect of the present invention integrated in its chromosome.

In another preferred embodiment, the host cell is a mammalian cell, and the mammal includes human and non-human mammals.

In another preferred embodiment, the host cell is selected from the group consisting of: HEK cells, photoreceptor cells (including cone cells and/or rod cells), other visual cells (such as bipolar cells, horizontal cells), (optic) nerve cells, and a combination thereof.

In another preferred embodiment, the host cell is selected from the group consisting of: rod cells, cone cells, light-giving bipolar cells, light-removing bipolar cells, horizontal cells, ganglion cells, amacrine cells, and a combination thereof.

In another preferred embodiment, the host cell is a photoreceptor cell (i.e., a photosensory cell).

In a sixth aspect of the present invention, it provides a use of the vector according to the third aspect of the present invention or the adeno-associated virus vector according to the fourth aspect of the present invention for the preparation of a formulation or composition for the treatment of an ocular disease and/or the restoration of vision or photosensitivity of a subject.

In another preferred embodiment, the formulation or composition is used to enlarge or restore the function of photoreceptor cells of the retina, restore the subject's vision (or photosensitivity), and/or treat a retinal degenerative disease.

In another preferred embodiment, the retinal degenerative disease is selected from the group consisting of: retinal dystrophy (such as rod dystrophy, rod cone dystrophy, cone rod dystrophy, cone dystrophy or macular dystrophy), retinal or macular degeneration, retinitis pigmentosa, other diseases caused by loss of ability of photoreceptor cells, and a combination thereof.

In another preferred embodiment, the formulation or composition is used to treat a retinitis pigmentosa disease, preferably a retinitis pigmentosa disease caused by PROM1 gene mutation.

In a seventh aspect of the present invention, it provides a pharmaceutical formulation comprising (a) the vector according to the third aspect of the present invention or the adeno-associated virus vector according to the fourth aspect of the present invention, and (b) a pharmaceutically acceptable carrier or excipient.

In another preferred embodiment, the dosage form of the pharmaceutical formulation is selected from the group consisting of: lyophilized formulations, liquid formulations, and a combination thereof.

In another preferred embodiment, the content of the vectors in the pharmaceutical formulation is $1\times10^9$-$1\times10^{16}$ viruses/ml, preferably $1\times10^1$-$1\times10^1$ viruses/ml.

In another preferred embodiment, the pharmaceutical formulation is used to treat eye diseases and/or restore the subject's vision or photosensitivity.

In another preferred embodiment, the eye disease is caused by PROM1 gene mutation.

In another preferred embodiment, the pharmaceutical formulation is used to enlarge or restore the function of photoreceptor cells of the retina, restore the subject's vision (or photosensitivity), and/or treat a retinal degenerative disease.

In another preferred embodiment, the pharmaceutical formulation is used to treat a retinitis pigmentosa disease, preferably a retinitis pigmentosa disease caused by PROM1 gene mutation.

In an eighth aspect of the present invention, it provides a therapeutic method comprising administering the vector according to the third aspect of the present invention or the adeno-associated virus vector according to the fourth aspect of the present invention to a subject in need.

In another preferred embodiment, the adeno-associated virus vector is introduced into the eye of the subject in need.

In another preferred embodiment, the subject in need includes human and non-human mammals.

In another preferred embodiment, the treatment method is a method for treating eye diseases.

In another preferred embodiment, the eye disease is caused by PROM1 gene mutation.

In another preferred embodiment, the ocular disease is a retinal degenerative disease, preferably a retinitis pigmentosa disease.

In another preferred embodiment, the retinal degenerative disease is selected from the group consisting of: retinal dystrophy (such as rod dystrophy, rod cone dystrophy, cone rod dystrophy, cone dystrophy or macular dystrophy), retinal or macular degeneration, retinitis pigmentosa, other diseases caused by loss of capacity of photoreceptor cells, and a combination thereof.

In another preferred embodiment, the treatment method is used to enlarge or restore the photoreceptor cell function of the retina and restore the subject's vision or photosensitivity.

In a ninth aspect of the present invention, it provides a method for preparing PROM1 protein, comprising culturing the host cell according to the fifth aspect of the present invention, thereby obtaining the PROM1 protein.

It should be understood that, within the scope of the present invention, the technical features specifically described above and below (such as the Examples) can be combined with each other, thereby constituting a new or preferred technical solution which needs not be described one by one.

DETAILED DESCRIPTION OF INVENTION

Figure 1:
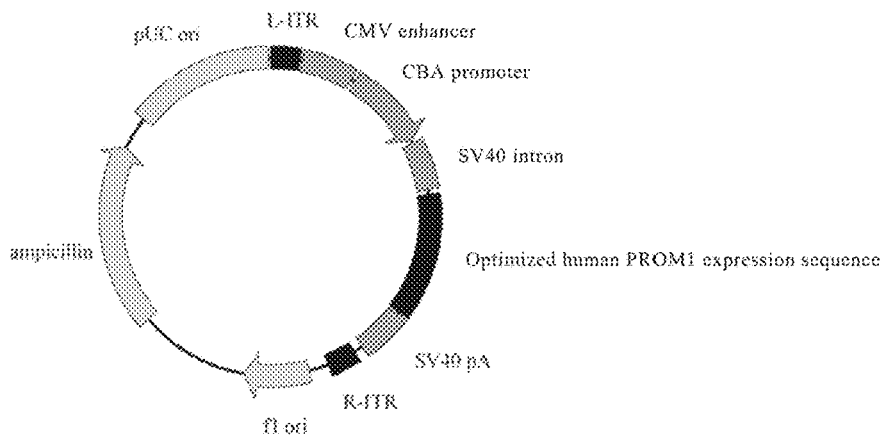
FIG. 1 shows a structural diagram of rAAV/CBA.opti-hPROM1 vector.

After extensive and intensive research, the PROM1 gene coding sequence was specially optimized to obtain a nucleotide sequence that is especially suitable for the efficient expression of the PROM1 protein in mammalian (such as human) cells (especially photoreceptor cells), and a recombinant AAV virus expressing normal human PROM1 protein was constructed, which was demonstrated to be effective in the PROM1 knockout mouse model. The experimental results showed that compared with the unoptimized coding sequence, the expression level of the specially optimized PROM1 coding sequence (SEQ ID NO: 1) was significantly increased by more than 3 times, which is very suitable for expression in mammalian (especially human) cells and can effectively treat eye diseases such as retinitis pigmentosa. On this basis, the present inventor has completed the present invention.

Terms

In order to understand the present invention more easily, some techniques and scientific terms are specifically defined below. As used in this application, each of the following terms shall have the meaning given below unless otherwise defined herein. Other definitions are stated throughout the application.

The term "about" may refer to a value or composition within an acceptable error range of a particular value or composition determined by a person of ordinary skill in the art, which will depend in part on how the value or composition is measured or determined. For example, as used herein, the expression "about 100" includes all values between 99 and 101 (e.g., 99.1, 99.2, 99.3, 99.4, etc.).

As used herein, the terms "include" or "comprise (comprising)" may be open, semi-enclosed, and enclosed. In other words, the term also includes "substantially consisting of" or "consisting of".

Sequence identity is determined by comparing two aligned sequences along a predetermined comparison window, which may be 50%, 60%, 70%, 80%, 90%, 95% or 100% of the length of the reference nucleotide sequence or protein, and determining the number of positions at which the same residue appears. Typically, it is expressed as a percentage. The measurement of sequence identity of nucleotide sequences is a method well known to those skilled in the art.

As used herein, the terms "subject" and "subject in need" refer to any mammal or non-mammal. Mammals include, but are not limited to, humans, vertebrates such as rodents, non-human primates, cattle, horses, dogs, cats, pigs, sheep, and goats.

As used herein, the terms "photoreceptor", "photosensory cell" and "photoreceptor cell" are used interchangeably, including rod cells and cone cells.

PROM1

As used herein, the terms "PROM1 protein", "polypeptide", "protein of the present invention", "human PROM1 protein" have the same meaning and are used interchangeably herein.

The protein encoded by PROM1 gene (PROM1 protein) is a transmembrane glycoprotein, which has been used as a biomarker of hematopoietic stem cells for a long time. It is expressed in many tissues of organisms. In retina, the encoded protein thereof is located at the base of the outer segment and connecting cilia of photoreceptor cells, which played an important role in the formation of the outer segment membrane disc of photoreceptor cells. In previous studies, PROM1 gene knockout mice can have RP-like disease manifestations, while mutant PROM1 gene knockin mice have abnormal development of the photoreceptor outer segment membrane disc.

Nucleic Acid Coding Sequence

The technical problem to be solved of the present invention is to overcome the technical defects of low expression amount of PROM1 and poor treatment effect in the prior art. The object of the present invention is to provide a PROM1 optimized gene sequence. The optimized PROM1 coding sequence of the present invention is shown in SEQ ID NO: 1, and the size thereof is 2505 bp. Through research, it is found that the PROM1 protein expression efficiency of the optimized PROM1 coding sequence (SEQ ID NO: 1) of the present invention is higher, and more PROM1 proteins play physiological roles in the patient's retinal photoreceptor cells.

The nucleotide sequence encoding the PROM1 protein of the present invention is shown in SEQ ID NO: 1. In another preferred embodiment, the nucleotide sequence is of ≥95%, preferably ≥98%, more preferably ≥99% homologous to the sequence as shown in SEQ ID NO: 1. In the present invention, the nucleic acid encoding the PROM1 protein is also referred to a PROM1 optimized gene, a PROM1 optimized nucleic acid or opti-hPROM1.

The polynucleotides of the present invention may be in the form of DNA or RNA. In another preferred embodiment, the nucleotide is DNA. DNA form includes cDNA, genomic DNA, or synthetic DNA. DNA can be single-stranded or double-stranded. DNA can be a coding strand or a non-coding strand. The nucleotide sequence of the present invention encodes the amino acid sequence shown in SEQ ID NO: 3.

NCBI reference sequence number of PROM1 protein is NP_001139322.1, and the amino acid sequence is as shown in SEQ ID NO: 3.

(SEQ ID NO: 3)

| | | | | | |
|---|---|---|---|---|---|
| 1 | malvlgslll | lglcgnsfsg | gqpsstdapk | awnyelpatn | yetqdshkag pigilfelvh |
| 61 | iflyvvqprd | fpedtlrkfl | qkayeskidy | dkpetvilgl | kivyyeagii lccvlgllfi |
| 121 | ilmplvgyff | cmcrccnkcg | gemhqrqken | gpflrkcfai | sllviciiis igifygfvan |
| 181 | hqvrtrikrs | rkladsnfkd | lrtllnetpe | qikyilaqyn | ttkdkaftdl nsinsvlggg |
| 241 | ildrlrpnii | pvldeiksma | taiketkeal | enmnstlksl | hqqstqlsss ltsvktslrs |
| 301 | slndplclvh | pssetcnsir | lslsqlnsnp | elrqlppvda | eldnvnnvlr tdldglvqqg |
| 361 | yqslndipdr | vqrqtttvva | gikrvlnsig | sdidnvtqrl | piqdilsafs vyvnntesyi |
| 421 | hrnlptleey | dsywwlgglv | icslltlivi | fyylgllcgv | cgydrhatpt trgcvsntgg |
| 481 | vflmvgvgls | flfcwilmii | vvltfvfgan | veklicepyt | skelfrvldt pyllnedwey |
| 541 | ylsgklfnks | kmkltfeqvy | sdckknrgty | gtlhlqnsfn | isehlnineh tgsisseles |
| 601 | lkvnlnifll | gaagrknlqd | faacgidrmn | ydsylaqtgk | spagvnllsf aydleakans |
| 661 | lppgnlrnsl | ktdaqtikti | hqqrvlpieq | slstlyqsvk | ilqrtngnll ervtrilasl |
| 721 | dfaqnfitnn | tssviieetk | kygrtiigyf | ehylqwiefs | isekvasckp vataldtavd |
| 781 | vflcsyiidp | lnlfwfgigk | atvfllpali | favklakyyr | rmdsedvydd psqh |

The nucleic acid sequence can be DNA, RNA, cDNA or PNA. The nucleic acid sequence can be genomic, recombinant or synthetic. The nucleic acid sequence can be isolated or purified. The nucleic acid sequence can be single-stranded or double-stranded. Preferably, the nucleic acid sequence will encode a PROM1 protein as described herein. Nucleic acid sequences can be derived by cloning, for example using standard molecular cloning techniques including restriction enzyme digestion, ligation, gel electrophoresis, such as described in Sambrook et al. Molecular Cloning: A laboratory manual, Cold Spring Harbour Laboratory Press). Nucleic acid sequences can be isolated, for example using PCR techniques. Isolation means the separation of a nucleic acid sequence from any impurities and from other nucleic acid sequences and/or proteins that are naturally found to associate with the nucleic acid sequence in its source. Preferably, it will also be free of cellular material, culture medium or other chemicals from the purification/production process. Nucleic acid sequences may be synthetic, for example by direct chemical synthesis. The nucleic acid sequence can be provided as a naked nucleic acid, or can be provided in complex with a protein or lipid.

Generally, the full-length nucleotide sequence or fragment thereof of the present invention can be obtained by PCR amplification method, recombination method or artificial synthesis method. For PCR amplification methods, primers can be designed according to the disclosed relevant nucleotide sequences, especially open reading frame sequences, and the relevant sequences can be amplified using commercially available cDNA libraries or cDNA libraries prepared according to conventional methods known to those skilled in the art as templates. When the sequence is long, it is often necessary to carry out two or more PCR amplifications, and then splice the amplified fragments together in the correct order. At present, DNA sequence encoding that polypeptide of the present invention (or fragments thereof, or derivative thereof) can be obtained entirely by chemical synthesis. The DNA sequence can then be introduced into various existing DNA molecules (or such as vectors) and cells known in the art.

The present invention also relates to vectors comprising polynucleotides of the present invention, and host cells produced by genetic engineering using the vector or polypeptide coding sequence of the present invention. The above polynucleotides, vectors or host cells may be isolated.

As used herein, "isolated" mean that a substance is separated from its original environment (if it is a natural substance, the original environment is the natural environment). For example, polynucleotides and polypeptides in the natural state in living cells are not isolated and purified, but the same polynucleotides or polypeptides are isolated and purified if they are separated from other substances existing in the natural state.

In a preferred embodiment of the present invention, the nucleotide sequence is shown in SEQ ID NO: 1.

Once the relevant sequences are obtained, the relevant sequences can be obtained in large quantities by recombination method. It is usually cloned into a vector, then transferred into a cell, and then the relevant sequence is isolated from the proliferated host cell by conventional methods.

In addition, the relevant sequences can also be synthesized by artificial synthesis, especially when the fragment length is short. Usually, fragments with long sequences can be obtained by synthesizing several small fragments first and then connecting them.

The method of amplifying DNA/RNA by PCR technology is preferably used to obtain the gene of the present invention. Primers used for PCR can be appropriately selected according to the sequence information of the present invention disclosed herein, and can be synthesized by conventional methods. Amplified DNA/RNA fragments can be isolated and purified by conventional methods such as gel electrophoresis.

The present invention also relates to vectors comprising polynucleotides of the present invention, host cells genetically engineered using the vector or protein coding sequence of the present invention, and methods for expressing PROM1 protein using said host cells by recombinant techniques.

Host cells (e.g., mammalian cells) expressing the PROM1 protein of the present invention can be obtained using the polynucleotide sequence of the present invention by conventional recombinant DNA techniques. Generally, it comprises the step of transferring the polynucleotide according to the first aspect of the invention or the vector according to the third aspect of the invention or the adeno-associated virus vector according to the fourth aspect of the invention into a host cell.

Methods well known to those skilled in the art can be used to construct expression vectors containing DNA sequences encoding polypeptides of the present invention and appropriate transcription/translation control signals. These methods include in vitro recombinant DNA technology, DNA synthesis technology, in vivo recombination technology, etc. The DNA sequence can be effectively linked to an appropriate promoter in the expression vector to guide mRNA synthesis. The expression vector also includes a ribosome binding site for translation initiation and a transcription terminator.

In addition, the expression vector preferably comprises one or more selectable marker genes to provide phenotypic traits for selecting transformed host cells, such as dihydrofolate reductase for eukaryotic cell culture, neomycin resistance and green fluorescent protein (GFP), or tetracycline or ampicillin resistance for *Escherichia coli*.

Vectors comprising the above-mentioned appropriate DNA sequences and appropriate promoters or control sequences can be used to transform appropriate host cells to enable them to express polypeptides.

Host cells can be prokaryotic cells, lower eukaryotic cells or higher eukaryotic cells, such as mammalian cells (including human and non-human mammals). Representative examples include: CHO, NS0, COS7, or 293-cells of animal cells, etc. In a preferred embodiment of the present invention, 293T cells, photoreceptor cells (including cone cells and/or rod cells), other visual cells (such as double ganglion cells), nerve cells are selected as host cells. In another preferred embodiment, the host cell is selected from the group consisting of: rod cells, cone cells, light-giving bipolar cells, light-removing bipolar cells, horizontal cells, ganglion cells, amacrine cells, and a combination thereof.

Transformation of host cells with recombinant DNA can be carried out using conventional techniques well known to those skilled in the art. When the host is a prokaryote such as *Escherichia coli*, competent cells capable of absorbing DNA can be harvested after the exponential growth period, using $CaCl_2$) method, the steps used are well known in the art. Another method is to use $MgCl_2$. If necessary, the transformation can also be carried out by electroporation. When the host is a eukaryote, the following DNA transfection methods can be selected from: calcium phosphate coprecipitation method, conventional mechanical methods such as microinjection, electroporation, liposome packaging, etc.

The obtained transformant can be cultured by conventional methods to express the protein encoded by the gene of the present invention. Depending on the host cell used, the medium used in the culture may be selected from a variety of conventional media. Culture under conditions suitable for the growth of host cells. After the host cells have grown to an appropriate cell density, the selected promoter is induced by a suitable method (such as temperature conversion or chemical induction), and the cells are cultured for a period of time.

The polypeptide in the above methods can be expressed intracellular, or on the cell membrane, or secreted outside the cell. If desired, proteins can be isolated and purified by various separation methods using their physical, chemical and other properties. These methods are well known to those skilled in the art. Examples of these methods include, but are not limited to, conventional renaturation processes, treatment with protein precipitant agent (salting-out method), centrifugation, osmotic bacteriolysis, supertreatment, ultracentrifugation, molecular sieve chromatography (gel filtration), adsorption chromatography, ion exchange chromatography, high performance liquid chromatography (HPLC) and other various liquid chromatography techniques, and combinations of these methods.

Sequence Optimization

In the present invention, an optimized coding sequence of PROM1 that is particularly suitable for expression in mammalian cells is provided, and the coding sequence is shown in SEQ ID NO: 1

As used herein, the "optimized PROM1 coding sequence" and "optimized PROM1 coding gene" refer to a nucleotide sequence used to encode PROM1, said nucleotide sequence encoding the amino acid sequence shown in SEQ ID NO: 3.

In the present invention, the wild DNA coding sequence (unoptimized DNA coding sequence) of PROM1 is shown in SEQ ID NO: 2, and the expression level of the unoptimized wild DNA coding sequence is very low.

The PROM1 wild coding sequence is derived from the NCBI reference sequence: coding region CDS (positions 213-2717) of NM_001145850.1, and the specific nucleic acid sequence is shown in SEQ ID NO: 2.

(SEQ ID NO: 2)
ATGGCCCTCGTACTCGGCTCCCTGTTGCTGCTGGGGCTGTGCGGGAACT

CCTTTTCAGGAGGGCAGCCTTCATCCACAGATGCTCCTAAGGCTTGGAA

TTATGAATTGCCTGCAACAAATTATGAGACCCAAGACTCCCATAAAGCT

GGACCCATTGGCATTCTCTTTGAACTAGTGCATATCTTTCTCTATGTGG

TACAGCCGCGTGATTTCCCAGAAGATACTTTGAGAAAATTCTTACAGAA

GGCATATGAATCCAAAATTGATTATGACAAGCCAGAAACTGTAATCTTA

GGTCTAAAGATTGTCTACTATGAAGCAGGGATTATTCTATGCTGTGTCC

TGGGGCTGCTGTTTATTATTCTGATGCCTCTGGTGGGGTATTTCTTTTG

TATGTGTCGTTGCTGTAACAAATGTGGTGGAGAAATGCACCAGCGACAG

AAGGAAAATGGGCCCTTCCTGAGGAAATGCTTTGCAATCTCCCTGTTGG

TGATTTGTATAATAATAAGCATTGGCATCTTCTATGGTTTTGTGGCAAA

TCACCAGGTAAGAACCCGGATCAAAAGGAGTCGGAAACTGGCAGATAGC

AATTTCAAGGACTTGCGAACTCTCTTGAATGAAACTCCAGAGCAAATCA

AATATATATTGGCCCAGTACAACACTACCAAGGACAAGGCGTTCACAGA

TCTGAACAGTATCAATTCAGTGCTAGGAGGCGGAATTCTTGACCGACTG

AGACCCAACATCATCCCTGTTCTTGATGAGATTAAGTCCATGGCAACAG

CGATCAAGGAGACCAAAGAGGCGTTGGAGAACATGAACAGCACCTTGAA

GAGCTTGCACCAACAAAGTACACAGCTTAGCAGCAGTCTGACCAGCGTG

AAAACTAGCCTGCGGTCATCTCTCAATGACCCTCTGTGCTTGGTGCATC

CATCAAGTGAAACCTGCAACAGCATCAGATTGTCTCTAAGCCAGCTGAA

TAGCAACCCTGAACTGAGGCAGCTTCCACCCGTGGATGCAGAACTTGAC

AACGTTAATAACGTTCTTAGGACAGATTTGGATGGCCTGGTCCAACAGG

GCTATCAATCCCTTAATGATATACCTGACAGAGTACAACGCCAAACCAC

GACTGTCGTAGCAGGTATCAAAAGGGTCTTGAATTCCATTGGTTCAGAT

ATCGACAATGTAACTCAGCGTCTTCCTATTCAGGATATACTCTCAGCAT

TCTCTGTTTATGTTAATAACACTGAAAGTTACATCCACAGAAATTTACC

TACATTGGAAGAGTATGATTCATACTGGTGGCTGGGTGGCCTGGTCATC

TGCTCTCTGCTGACCCTCATCGTGATTTTTACTACCTGGGCTTACTGT

GTGGCGTGTGCGGCTATGACAGGCATGCCACCCCGACCACCCGAGGCTG

TGTCTCCAACACCGGAGGCGTCTTCCTCATGGTTGGAGTTGGATTAAGT

TTCCTCTTTTGCTGGATATTGATGATCATTGTGGTTCTTACCTTTGTCT

TTGGTGCAAATGTGGAAAAACTGATCTGTGAACCTTACACGAGCAAGGA

ATTATTCCGGGTTTTGGATACACCCTACTTACTAAATGAAGACTGGGAA

TACTATCTCTCTGGGAAGCTATTTAATAAATCAAAAATGAAGCTCACTT

TTGAACAAGTTTACAGTGACTGCAAAAAAAATAGAGGCACTTACGGCAC

TCTTCACCTGCAGAACAGCTTCAATATCAGTGAACATCTCAACATTAAT

GAGCATACTGGAAGCATAAGCAGTGAATTGGAAAGTCTGAAGGTAAATC

TTAATATCTTTCTGTTGGGTGCAGCAGGAAGAAAAAACCTTCAGGATTT

TGCTGCTTGTGGAATAGACAGAATGAATTATGACAGCTACTTGGCTCAG

ACTGGTAAATCCCCCGCAGGAGTGAATCTTTTATCATTTGCATATGATC

TAGAAGCAAAAGCAAACAGTTTGCCCCCAGGAAATTTGAGGAACTCCCT

GAAAAGAGATGCACAAACTATTAAAACAATTCACCAGCAACGAGTCCTT

CCTATAGAACAATCACTGAGCACTCTATACCAAAGCGTCAAGATACTTC

AACGCACAGGGAATGGATTGTTGGAGAGAGTAACTAGGATTCTAGCTTC

TCTGGATTTTGCTCAGAACTTCATCACAAACAATACTTCCTCTGTTATT

ATTGAGGAAACTAAGAAGTATGGGAGAACAATAATAGGATATTTTGAAC

ATTATCTGCAGTGGATCGAGTTCTCTATCAGTGAGAAAGTGGCATCGTG

CAAACCTGTGGCCACCGCTCTAGATACTGCTGTTGATGTCTTTCTGTGT

AGCTACATTATCGACCCCTTGAATTTGTTTTGGTTTGGCATAGGAAAAG

CTACTGTATTTTTACTTCCGGCTCTAATTTTTGCGGTAAAACTGGCTAA

GTACTATCGTCGAATGGATTCGGAGGACGTGTACGATGACCCATCACAA

CATTGA

The present invention optimizes the sequence fragments that affect gene expression. These sequence fragments include, but are not limited to, codon usage preference, elimination of secondary structures that are not conducive to expression (such as hairpin structures), changes in GC content, CpG dinucleotide content, mRNA secondary structures, and concealed splice sites, early polyadenylation sites, internal ribosome entry and binding sites, negative CpG islands, RNA unstable regions, repeat sequences (direct repeats, inverted repeats, etc.) and restriction sites that may affect cloning. Through analysis and experimental screening, a specially optimized DNA coding sequence as shown in SEQ ID NO: 1 was finally obtained. The similarity between the coding sequence of SEQ ID NO: 1 and the wild coding sequence of SEQ ID NO: 2 is 75% (1879/2505).

(SEQ ID NO: 1)
ATGGCCCTGGTGCTGGGGAGCCTGCTGCTGCTGGGGCTGTGCGGAAA

CTCCTTCTCCGGGGCCAGCCCTCCAGCACCGACGCTCCTAAGGCCTGGA

ACTACGAGCTGCCCGCCACCAACTACGAAACCCAAGACTCCCACAAAGC

CGGCCCCATCGGCATCCTGTTCGAACTCGTGCATATTTTCCTCTACGTGGT

TCAACCCAGAGATTTTCCCGAGGACACCCTGAGAAAGTTCCTGCAGAAGG

CCTATGAGAGCAAGATTGACTACGACAAGCCCGAAACCGTGATCCTGGG

CCTGAAGATCGTGTATTATGAGGCCGAATTATCCTCTGTTGCGTGCTGG

GCCTGCTGTTTATCATCCTGATGCCACTGGTGGGCTACTTCTTTTGCATGT

GCAGATGTTGCAACAAGTGTGGCGGCGAGATGCACCAGCGTCAGAAGGA

GAACGGGCCTTTCCTCCGGAAATGCTTTGCCATCTCCCTGCTGGTGATTTG

```
TATCATTATCAGCATCGGGATCTTCTACGGATTCGTGGCTAACCATCAGG

TCAGAACCCGCATCAAGCGCAGTAGAAAGCTGGCCGACTCCAACTTCAA

GGACCTGCGGACCCTGCTGAACGAGACCCCCGAGCAGATCAAGTACATTC

TGGCCCAATACAACACCACCAAGGACAAAGCCTTCACAGACCTGAACTCC

ATCAACAGCGTGCTCGGCGGAGGCATACTGGACCGGCTGAGACCCAACA

TAATACCCGTGCTGGACGAAATCAAAAGCATGGCCACCGCCATAAAGGA

GACCAAAGAAGCCCTCGAAAACATGAACTCCACCCTGAAAAGCCTCCAC

CAACAAAGCACCCAGCTCAGCAGCTCCCTGACCAGCGTGAAAACAAGCC

TGAGAAGCAGCCTGAACGACCCCCTGTGCCTCGTCCACCCCAGCAGCGAG

ACCTGCAACAGCATCAGACTCAGCCTCAGCCAACTCAACAGCAACCCCGA

ACTCAGACAACTCCCCCCGTGGACGCCGAACTGGACAACGTCAACAAC

GTGCTCAGAACAGACCTGGACGGCCTCGTGCAGCAGGGCTACCAAAGCC

TCAACGACATCCCCGACAGAGTGCAGAGACAAACCACCACCGTGGTGGC

CGGAATTAAGAGAGTCCTGAATAGCATCGGCAGCGACATTGACAACGTG

ACACAAAGACTCCCCATCCAAGACATACTGAGCGCCTTCAGTGTGTACGT

CAACAACACCGAGAGTTACATACACAGAAACCTGCCCACCCTGGAGGAG

TACGACAGCTACTGGTGGCTGGGCGGACTCGTCATCTGCAGCCTCCTGAC

CCTGATCGTGATTTTCTATTACCTGGGCCTGCTCTGCGGCGTCTGCGGCTA

CGACCGACACGCCACACCCACCACAAGGGGCTGCGTGTCTAATACCGGC

GGCGTGTTCCTCATGGTGGGCGTCGGACTGTCCTTCCTGTTCTGTTGGATC

CTGATGATTATTGTTGTGCTGACCTTCGTTTTCGGCGCCAACGTGGAGAA

GCTGATCTGCGAGCCCTACACCTCCAAAGAGCTGTTCAGAGTGCTGGACA

CCCCCTATCTGCTGAACGAAGACTGGGAGTATTACCTGAGCGGCAAGCTG

TTTAATAAGAGTAAGATGAAACTGACCTTCGAGCAGGTGTATAGCGACTG

CAAGAAAAACCGCGGAACCTACGGCACCCTGCACCTGCAGAACAGCTTC

AACATTTCAGAGCACCTCAACATCAACGAGCACACCGGCTCCATCAGGAG

CGAACTGGAGAGCCTGAAGGTGAACCTGAACATCTTCCTGCTGGGCGCCG

CAGGCAGAAAAAACCTGCAGGACTTCGCCGCCTGCGGCATCGACAGAAT

GAACTACGACAGCTACCTGGCCCAGACCGGCAAGAGCCCCGCCGGCGTG

AACCTGCTGAGCTTCGCCTACGACCTGGAGGCCAAGGCCAACAGCCTGCC

CCCCGGCAACCTGAGAAACAGCCTGAAGAGAGACGCCCAGACCATCAAG

ACCATCCACCAGCAGAGTGCTGCCCATCGAGCAGAGCCTGAGCACCCT

GTACCAGAGCGTGAAGATCCTGCAGAGAACCGGCAACGGCCTGCTGGAG

AGAGTGACCAGAATCCTGGCCAGCCTGGACTTCGCCCAGAACTTCATCAC

CAACAACACCAGCAGCGTGATCATCGAGGAGACCAAGAAGTACGGCAGA

ACCATCATCGCCTACTTCGAGCACTACCTGCAGTGGATCGAGTTCAGCAT

CAGCGAGAAGGTGGCCAGCTGCAAGCCCGTGGCCACCGCCCTGGACACC

GCCGTGGACGTGTTCCTGTGCAGCTACATCATCGACCCCCTGAACCTGTT

CTGGTTCGGCATCGGCAAGGCCACCGTGTTCCTGCTGCCCGCCCTGATCTT

CGCCGTGAAGCTGGCCAAGTACTACAGAAGAATGGACAGCGAGGACGTG

TACGACGACCCCAGCCAGCACTGA
```

Adeno-Associated Virus

Compared with other viral vectors, adeno-associated viruses (AAV) are smaller, non-pathogenic, and capable of transfecting dividing and non-dividing cells. Therefore, gene therapy based on AAV vectors for ocular diseases, especially hereditary retinal degeneration, has attracted extensive attention.

Adeno-associated virus (AAV), also known as adeno associated virus, belongs to the family Parvoviridae and the genus Dependovirus. It is the simplest single-stranded DNA-deficient virus found so far, and requires helper viruses (usually adenoviruses) to participate in replication. It encodes cap and rep genes in the inverted repeat sequence (ITR) at both ends. ITRs play a decisive role in virus replication and packaging. Cap gene encodes virus capsid protein, and rep gene participates in virus replication and integration. AAV can infect a variety of cells.

Recombinant adeno-associated virus vector (rAAV) is derived from non-pathogenic wild-type adeno-associated virus. Due to its good safety, wide range of host cells (divided and non-divided cells), low immunogenicity, and long time to express foreign genes in vivo, it is regarded as one of the most promising gene transfer vectors and has been widely used in gene therapy and vaccine research worldwide. After more than 10 years of research, the biological characteristics of recombinant adeno-associated virus have been deeply understood, especially in terms of its application effects in various cells, tissues and in vivo experiments, in which a lot of information have been accumulated. In medical research, rAAV is used in gene therapy for various diseases (including in vivo and in vitro experiments). At the same time, as a characteristic gene transfer vector, it is also widely used in gene function research, disease model construction, gene knockout mouse preparation, etc.

In a preferred embodiment of the present invention, the vector is a recombinant AAV vector. AAVs are relatively small DNA viruses that can be integrated into the genome of the cells they infect in a stable and site-specific manner. They can infect a wide range of cells without any effect on cell growth, morphology or differentiation, and they do not seem to be involved in human pathology. AAV genome has been cloned, sequenced and characterized. AAV contains inverted terminal repeat (ITR) regions of about 145 bases at each end, which serve as the origin of replication of the virus. The rest of the genome is divided into two important regions with encapsidation functions: the left portion of the genome containing the rep gene involved in viral replication and viral gene expression; and the right portion of the genome comprising the cap gene encoding the viral capsid protein.

AAV vectors can be prepared using standard methods in the art. Any serotype of adeno-associated virus is suitable. Methods for purifying vectors can be found, for example, in U.S. Pat. Nos. 6,566,118, 6,989,264 and 6,995,006, the disclosures of which are incorporated herein by reference in their entirety. The preparation of hybrid vectors is described, for example, in PCT application No. PCT/US2005/027091, the disclosure of which is incorporated herein by reference in its entirety. The use of AAV-derived vectors for transporting genes in vitro and in vivo has been described (see, for example, International Patent Application Publication Nos. WO 91/18088 and WO 93/09239; U.S. Pat. Nos.

4,797,368, 6,596,535 and 5,139,941, and European Pat. No. 0488,528, which are incorporated herein by reference in their entirety). These patent publications describe various constructs derived from AAV in which the rep and/or cap genes are deleted and replaced by the gene of interest, and the use of these constructs to transport the gene of interest in vitro (into cultured cells) or in vivo (directly into organisms). Replication-deficient recombinant AAV can be prepared by co-transfecting the following plasmids into cell lines infected by human helper viruses (such as adenoviruses): plasmids containing nucleic acid sequences of interest flanked by two AAV inverted terminal repeat (ITR) regions, and plasmids carrying AAV capsizing genes (rep and cap genes). The resulting AAV recombinant was then purified by standard techniques.

In some embodiments, the recombinant vector is capsized into viral particles (for example, AAV virus particles including but not limited to AAV1, AAV2, AAV3, AAV4, AAV5, AAV6, AAV7, AAV8, AAV9, AAV10, AAV 11, AAV12, AAV13, AAV14, AAV15 and AAV16). Accordingly, the present disclosure includes recombinant viral particles (recombinant because they contain recombinant polynucleotides) comprising any of the vectors described herein. Methods of producing such particles are known in the art and are described in U.S. Pat. No. 6,596,535.

Expression Vectors and Host Cells

The invention also provides an expression vector for PROM1 protein, which contains the optimized PROM1 coding sequence of the present invention.

With the provided sequence information, those skilled in the art can use available cloning techniques to produce nucleic acid sequences or vectors suitable for transduction into cells.

Preferably, a nucleic acid sequence encoding the PROM1 protein is provided as a vector, preferably an expression vector. Preferably, it can be provided as a gene therapy vector preferably suitable for transduction and expression in retinal target cells. The vector may be viral or non-viral (e.g., plasmid). Viral vectors include those derived from adenoviruses, adeno-associated virus (AAV) including mutated forms, retroviruses, lentiviruses, herpes viruses, vaccinia viruses, MMLV, GaLV, simian immunodeficiency virus (SIV), HIV, poxvirus and SV40. Preferably, the viral vector is replication defective, although it is envisaged that it may be replication deficient, replicable or conditionally replicable. Viral vectors can usually maintain an extrachromosomal state without integrating into the genome of target retinal cells. Preferred viral vectors for introducing nucleic acid sequences encoding PROM1 protein into retinal target cells are AAV vectors, such as self-complementary adeno-associated virus (scAAV). Selective targeting can be achieved using specific AAV serotypes (AAV serotype 2 to AAV serotype 12) or modified versions of any of these serotypes (including AAV 4YF and AAV 7m8 vectors).

Viral vectors can be modified to delete any unnecessary sequences. For example, in AAV, the virus may be modified to delete all or part of the IX gene, Ela and/or Elb gene. For wild-type AAV, replication is very inefficient without the presence of helper viruses such as adenoviruses. For the recombinant adeno-associated virus, preferably, the replication gene and capsid gene are provided in trans (in the pRep/Cap plasmid), and only the 2ITR of the AAV genome is retained and packaged into the virion, while the required adenovirus gene is provided by the adenovirus or another plasmid. Similar modifications can also be made to lentiviral vectors.

Viral vectors have the ability to enter cells. However, non-viral vectors, such as plasmids, may be complexed with agents to facilitate the uptake of viral vectors by target cells. Such agents include polycationic agents. Alternatively, delivery systems such as liposome-based delivery systems may be used. The vector for use in the present invention is preferably suitable for use in vivo or in vitro, and preferably suitable for use in humans.

The vector will preferably comprise one or more regulatory sequences to direct the expression of the nucleic acid sequence in the retinal target cells. Regulatory sequences may include promoters, introns, enhancers, transcription termination signals, polyadenylation sequences, origin of replication, nucleic acid restriction sites, and homologous recombination sites operably linked to nucleic acid sequences. The vector may also include selectable markers, for example, to determine the expression of the vector in a growth system (e.g., bacterial cells) or in retinal target cells.

"Operably linked" means that sequences of nucleic acids are functionally related to sequences of which they are operably linked so that they are linked in a way that allows them to affect each other's expression or function. For example, the nucleic acid sequence operably linked to the promoter will have an expression pattern influenced by the promoter.

The promoter mediates the expression of the nucleic acid sequence to which it is linked. The promoter may be constitutive or may be inducible. Promoters can direct ubiquitous expression in inner retinal cells or specific expression in neuron. In the latter case, the promoter can direct cell type-specific expression, for example to optic ganglion cells. Suitable promoters will be known to those skilled in the art. For example, suitable promoters may be selected from the group consisting of L7, thy-1, restoring protein, calbindin, human CMV, GAD-67, chicken β actin, hSyn, Grm6, Grm6 enhancer SV40 fusion protein. Targeting can be achieved using cell-specific promoters, such as Grm6-SV40 for selective targeting to optic nerve cells. The Grm6 promoter is a fusion of the 200 base pair enhancer sequence of the Grm6 gene and the eukaryotic promoter of SV40. The Grm6 gene encodes a metabotropic glutamate receptor mGluR6 specific to optic nerve cells. Preferred sources of the Grm6 gene are mice and humans. Ubiquitous expression can be achieved using pan-neuron promoters, examples of which are known and available in the art. One such example is CAG. The CAG promote is a fusion of CMV early enhancer and chicken β actin promoter.

One example of a suitable promoter is an immediate early cytomegalovirus (CMV) promoter sequence. The promoter sequence is a strongly constitutive promoter sequence capable of driving high-level expression of any polynucleotide sequence operably linked thereto. Another example of a suitable promoter is elongation growth factor-1α (EF-1α). However, other constitutive promoter sequences may also be used, including but not limited to the simian virus 40 (SV40) early promoter, the mouse mammary tumor virus (MMTV), the human immunodeficiency virus (HIV) long terminal repeat (LTR) promoter, the MoMuLV promoter, the avian leukemia virus promoter, the Epstein-Barr virus immediate early promoter, the Ruth's sarcoma virus promoter, and the human gene promoter, such as, but not limited to, actin promoter, myosin promoter, heme promoter and creatine kinase promoter. Further, the present invention should not be limited to the use of constitutive promoters. Inducible promoters are also contemplated as part of the present invention. The use of the inducible promoters provides a molecular switch capable of turning on expression of a polynucleotide sequence operably linked to the inducible promoter when such expression is desired, or turning off expression when expression is undesired. Examples of inducible promoters include, but are not limited to, metallothionein promoter, glucocorticoid promoter, progesterone promoter, and tetracycline promoter.

Many expression vectors can use PROM1 protein to express in mammalian cells (preferably human, more preferably human optic nerve cells or photoreceptor cells). The adeno-associated virus is preferably used in the present invention as an expression vector.

The present invention also provides a method for constructing a recombinant adeno-associated virus vector with a PROM1 optimized coding sequence, which can quickly and easily construct a recombinant adeno-associated virus vector carrying a PROM1 optimized coding sequence, and package to obtain a complex defective adeno-associated virus vector.

In another preferred embodiment, the sequence of the adeno-associated virus vector carrying the PROM1 optimized coding sequence of the present invention is shown in SEQ ID NO: 4. Wherein positions 1-141 are left ITR sequences; positions 153-532 are CMV enhancers (underlined part); positions 535-810 are chickens β actin promoter (italic part); positions 813-1006 are SV40 intron (double underlined portion); positions 1019-3523 are the optimized human PROM1 coding sequence (bold part); positions 3530-3757 are SV40 PolyA; positions 3758-3898 are right ITR sequence.

```
                                                   (SEQ ID NO: 4)
CCTGCAGGCAGCTGCGCGCTCGCTCGCTCACTGAGGCCGCCCGGGCAAAGCCCGGGCG

TCGGGCGACCTTTGGTCGCCCGGCCTCAGTGAGCGAGCGAGCGCGCAGAGAGGGAGTGGCC

AACTCCATCACTAGGGGTTCCTGCGGCCGCGTCGACATTGATTATTGACTAGTTATTAATAGT

AATCAATTACGGGGTCATTAGTTCATAGCCCATATATGGAGTTCCGCGTTACATAACTTACGG

TAAATGGCCCGCCTGGCTGACCGCCCAACGACCCCCGCCCATTGACGTCAATAATGACGTAT

GTTCCCATAGTAACGCCAATAGGGACTTTCCATTGACGTCAATGGGTGGACTATTTACGGTA

AACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTT

GGCAGTACATCTACGTATTAGTCATCGCTATTACCATGGGTCGAGGTGAGCCCCACGTTCTGCT

TCACTCTCCCCATCTCCCCCCCCTCCCCACCCCCAATTTTGTATTTATTTATTTTTAATTATTTTGTG

CAGCGATGGGGGCGGGGGGGGGGGGGCGCGCGCCAGGCGGGGCGGGGCGGGGCGAGGGGC

GGGGCGGGGCGAGGCGGAGAGGTGCGGCGGCAGCCAATCAGAGCGGCGCGCTCCGAAAGTTTC

CTTTTATGGCGAGGCGGCGGCGGCGGCGGCCCTATAAAAAGCGAAGCGCGCGGCGGGCGtctagag gatccggtactagaggaactgaaaaaccagaaagttaactggtaagtttagtcttttttgtcttttat ttcaggtcccggatccggtggtggtgcaaatcaaagaactgctcctcagtggatgttgcctttactt ctaggcctgtacggaagtgttacttctgctctaaaagctgcggaattgtacccgcacttctaggcct gtacggaagtgttacttctgctctaaaagctgcggaattgtacccgcgggaattccaccA

TGGCCCTGGTGCTGGGGAGCCTGCTGCTGCTGGGGCTGTGCGGAAACTCCTTCTCCGG

GGGCCAGCCCTCCAGCACCGACGCTCCTAAGGCCTGGAACTACGAGCTGCCCGCCACC

AACTACGAAACCCAAGACTCCCACAAAGCCGGCCCCATCGGCATCCTGTTCGAACTCGT

GCATATTTTCCTCTACGTGGTTCAACCCAGAGATTTTCCCGAGGACACCCTGAGAAAGT

TCCTGCAGAAGGCCTATGAGAGCAAGATTGACTACGACAAGCCCGAAACCGTGATCCT

GGGCCTGAAGATCGTGTATTATGAGGCCGGAATTATCCTCTGTTGCGTGCTGGGCCTGC

TGTTTATCATCCTGATGCCACTGGTGGGCTACTTCTTTTGCATGTGCAGATGTTGCAAC

AAGTGTGGCGGCGAGATGCACCAGCGTCAGAAGGAGAACGGGCCTTTCCTCCGGAAAT

GCTTTGCCATCTCCCTGCTGGTGATTTGTATCATTATCAGCATCGGGATCTTCTACGGAT

TCGTGGCTAACCATCAGGTCAGAACCCGCATCAAGCGCAGTAGAAAGCTGGCCGACTC

CAACTTCAAGGACCTGCGGACCCTGCTGAACGAGACCCCCGAGCAGATCAAGTACATTC

TGGCCCAATACAACACCACCAAGGACAAAGCCTTCACAGACCTGAACTCCATCAACAGC

GTGCTCGGCGGAGGCATACTGGACCGGCTGAGACCCAACATAATACCCGTGCTGGACG

AAATCAAAAGCATGGCCACCGCCATAAAGGAGACCAAAGAAGCCCTCGAAAACATGAA
```

CTCCACCCTGAAAAGCCTCCACCAACAAAGCACCCAGCTCAGCAGCTCCCTGACCAGCG

TGAAAACAAGCCTGAGAAGCAGCCTGAACGACCCCCTGTGCCTCGTCCACCCCAGCAG

CGAGACCTGCAACAGCATCAGACTCAGCCTCAGCCAACTCAACAGCAACCCCGAACTCA

GACAACTCCCCCCCGTGGACGCCGAACTGGACAACGTCAACAACGTGCTCAGAACAGA

CCTGGACGGCCTCGTGCAGCAGGGCTACCAAAGCCTCAACGACATCCCCGACAGAGTG

CAGAGACAAACCACCACCGTGGTGGCCGGAATTAAGAGAGTCCTGAATAGCATCGGCA

GCGACATTGACAACGTGACACAAAGACTCCCCATCCAAGACATACTGAGCGCCTTCAGT

GTGTACGTCAACAACACCGAGAGTTACATACACAGAAACCTGCCCACCCTGGAGGAGTA

CGACAGCTACTGGTGGCTGGGCGGACTCGTCATCTGCAGCCTCCTGACCCTGATCGTG

ATTTTCTATTACCTGGGCCTGCTCTGCGGCGTCTGCGGCTACGACCGACACGCCACACC

CACCACAAGGGGCTGCGTGTCTAATACCGGCGGCGTGTTCCTCATGGTGGGCGTCGGA

CTGTCCTTCCTGTTCTGTTGGATCCTGATGATTATTGTTGTGCTGACCTTCGTTTTCGGC

GCCAACGTGGAGAAGCTGATCTGCGAGCCCTACACCTCCAAAGAGCTGTTCAGAGTGC

TGGACACCCCCTATCTGCTGAACGAAGACTGGGAGTATTACCTGAGCGGCAAGCTGTTT

AATAAGAGTAAGATGAAACTGACCTTCGAGCAGGTGTATAGCGACTGCAAGAAAAACC

GCGGAACCTACGGCACCCTGCACCTGCAGAACAGCTTCAACATTTCAGAGCACCTCAAC

ATCAACGAGCACACCGGCTCCATCAGCAGCGAACTGGAGAGCCTGAAGGTGAACCTGA

ACATCTTCCTGCTGGGCGCCGCAGGCAGAAAAAACCTGCAGGACTTCGCCGCCTGCGG

CATCGACAGAATGAACTACGACAGCTACCTGGCCCAGACCGGCAAGAGCCCCGCCGGC

GTGAACCTGCTGAGCTTCGCCTACGACCTGGAGGCCAAGGCCAACAGCCTGCCCCCCG

GCAACCTGAGAAACAGCCTGAAGAGAGACGCCCAGACCATCAAGACCATCCACCAGCA

GAGAGTGCTGCCCATCGAGCAGAGCCTGAGCACCCTGTACCAGAGCGTGAAGATCCTG

CAGAGAACCGGCAACGGCCTGCTGGAGAGAGTGACCAGAATCCTGGCCAGCCTGGACT

TCGCCCAGAACTTCATCACCAACAACACCAGCAGCGTGATCATCGAGGAGACCAAGAA

GTACGGCAGAACCATCATCGGCTACTTCGAGCACTACCTGCAGTGGATCGAGTTCAGCA

TCAGCGAGAAGGTGGCCAGCTGCAAGCCCGTGGCCACCGCCCTGGACACCGCCGTGGA

CGTGTTCCTGTGCAGCTACATCATCGACCCCCTGAACCTGTTCTGGTTCGGCATCGGCA

AGGCCACCGTGTTCCTGCTGCCCGCCCTGATCTTCGCCGTGAAGCTGGCCAAGTACTAC

AGAAGAATGGACAGCGAGGACGTGTACGACGACCCCAGCCAGCACTGActcgagcgcggatcca gacatgataagatacattgatgagtttggacaaaccacaactagaatgcagtgaaaaaaatgctttattt gtgaaatttgtgatgctattgctttatttgtaaccattataagctgcaataaacaagttaacaacaacaa ttgcattcattttatgtttcaggttcagggggaggtgtgggaggttttttagtcgactggggaga gatctGCGGCCGCAGGAACCCCTAGTGATGGAGTTGGCCACTCCCTCTCTGCGCGCTCGCTCGCT

CACTGAGGCCGGGCGACCAAAGGTCGCCCGACGCCCGGGCTTTGCCCGGGCGGCCTCAGTGA

GCGAGCGAGCGCGCAGCTGCCTGCAGGGGCGCCTGATGCGGTATTTTCTCCTTACGCATCTG

TGCGGTATTTCACACCGCATACGTCAAAGCAACCATAGTACGCGCCCTGTAGCGGCGCATTA

AGCGCGGCGGGTGTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTCCCCGTCAAGCTCTA

AATCGGGGGCTCCCTTTAGGGTTCCGATTTAGTGCTTTACGGCACCTCGACCCCAAAAAACTT

GATTTGGGTGATGGTTCACGTAGTGGGCCATCGCCCTGATAGACGGTTTTTCGCCCTTTGACG

-continued

```
TTGGAGTCCACGTTCTTTAATAGTGGACTCTTGTTCCAAACTGGAACAACACTCAACCCTATC
TCGGGCTATTCTTTTGATTTATAAGGGATTTTGCCGATTTCGGCCTATTGGTTAAAAAATGAG
CTGATTTAACAAAAATTTAACGCGAATTTTAACAAAATATTAACGTTTACAATTTTATGGTGC
ACTCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGAGACGAAAG
GGCCTCGTGATACGCCTATTTTTATAGGTTAATGTCATGATAATAATGGTTTCTTAGACGTCA
GGTGGCACTTTTCGGGGAAATGTGCGCGGAACCCCTATTTGTTTATTTTTCTAAATACATTCA
AATATGTATCCGCTCATGAGACAATAACCCTGATAAATGCTTCAATAATATTGAAAAAGGAA
GAGTATGAGTATTCAACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATCAGTTGGGTGCACG
AGTGGGTTACATCGAACTGGATCTCAACAGCGGTAAGATCCTTGAGAGTTTTCGCCCCGAAG
AACGTTTTCCAATGATGAGCACTTTTAAAGTTCTGCTATGTGGCGCGGTATTATCCCGTATTG
ACGCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTGC
CATAACCATGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAATGGCAA
CAACGTTGCGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACTGG
GGCCAGATGGTAAGCCCTCCCGTATCGTAGTTATCTACACGACGGGGAGTCAGGCAACTATG
GATGAACGAAATAGACAGATCGCTGAGATAGGTGCCTCACTGATTAAGCATTGGTAACTGTC
AGACCAAGTTTACTCATATATACTTTAGATTGATTTAAAACTTCATTTTTAATTTAAAAGGAT
CTAGGTGAAGATCCTTTTTGATAATCTCATGACCAAAATCCCTTAACGTGAGTTTTCGTTCCA
CTGAGCGTCAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTC
CTTCTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGCA
CACAGCCCAGCTTGGAGCGAACGACCTACACCGAACTGAGATACCTACAGCGTGAGCTATGA
GAAAGCGCCACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGGAGCCTA
TGGAAAAACGCCAGCAACGCGGCCTTTTTACGGTTCCTGGCCTTTTGCTGGCCTTTTGCTCAC
ATGT
```

The invention also provides a host cell for expressing PROM1 protein. Preferably, the host cell is a mammalian cell (preferably a human, more preferably a human optic nerve cell or a photoreceptor cell), and the expression amount of the PROM1 protein is increased.

Preparations and Compositions

The present invention provides a formulation or composition comprising (a) the vector according to the third aspect of the invention or the adeno-associated virus vector according to the fourth aspect of the invention, and (b) a pharmaceutically acceptable carrier or excipient.

In another preferred embodiment, the pharmaceutical formulation is used to treat an eye disease, which is an eye disease caused by the mutation in the PROM1 gene.

In another preferred embodiment, the pharmaceutical formulation is used to treat retinitis pigmentosa (RP), preferably retinitis pigmentosa caused by mutations in the PROM1 gene.

The "active ingredient" in the pharmaceutical composition of the present invention refers to the vector of the present invention, such as a viral vector (including adeno-associated virus vector). The "active ingredient", the formulation and/or composition of the present invention can be used to treat an eye disease. "Safe and effective amount" refer to an amount of that active ingredient sufficient to significantly improve the condition or symptoms without causing serious side effects. "Pharmaceutically acceptable carrier or excipient" refers to one or more compatible solid or liquid fillers or gel substances, which are suitable for human use and must have sufficient purity and low toxicity. "Compatibility" herein means that the ability of each component of the composition to blend with the active ingredient of the present invention and with each other without significantly reducing the efficacy of the active ingredient.

The composition may be a liquid or a solid, such as a powder, gel or paste. Preferably, the composition is a liquid, preferably an injectable liquid. Suitable excipients will be known to those skilled in the art.

In the present invention, the carrier can be administered to the eye by subretinal or intravitreal administration. In each mode of administration, the carrier is preferably provided as an injectable liquid. Preferably, the injectable liquid is provided as a capsule or syringe.

Some examples of pharmaceutically acceptable carriers are cellulose and its derivatives (such as sodium carboxymethyl cellulose, sodium ethylcellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween*), wetting agents (such as sodium dodecyl sulfate), colorants, flavoring agents, stabilizers, antioxidants, preservatives, pyrogen-free water, etc.

The composition may comprise a physiologically acceptable sterile aqueous or anhydrous solution, dispersion, suspension or emulsion, and a sterile powder for redissolving into a sterile injectable solution or dispersion. Suitable aqueous and non-aqueous carriers, diluents, solvents or excipients include water, ethanol, polyols and suitable mixtures thereof.

The nucleic acid or fusion nucleic acid encoding PROM1 provided by the present invention can produce PROM1 protein in vitro or in vivo, and the preparation containing the optimized coding sequence of PROM1 can be applied to prepare drugs for treating eye diseases.

The optimized nucleic acid encoding the human PROM1 protein has a higher expression level, thereby translating more PROM1 protein, and expressing more PROM1 protein than the prior art, and can better treat retinitis pigmentosa.

Treatment

The present invention provides a method of providing photoreceptor function to cells, the method comprising introducing a vector comprising an optimized sequence encoding PROM1 into the eye. The method may include administering a nucleic acid vector to the inner retinal cells of the eye subretinal or intravitreal.

The present invention provides a nucleic acid vector for use in a method of treating retinal degeneration by providing photoreceptor function to cells, the nucleic acid vector comprising an optimized sequence encoding PROM1. The composition of the present invention can be administered alone or in combination with other therapeutic drugs (e.g., formulated in the same pharmaceutical composition).

The invention also provides a method for expanding the function of photoreceptor cells in the retina, in particular after rod and/or cone cell degeneration, the method comprising introducing a nucleic acid vector into the vitreous cavity of the eye, and the nucleic acid vector comprises an optimized sequence encoding PROM1. The method may include subretinal or intravitreal administering a nucleic acid vector to the inner retinal cells of the eye. The present invention provides a nucleic acid vector for use in the treatment of retinal degeneration by expanding the function of photoreceptor cells in the retina, and the nucleic acid vector comprises an optimized sequence encoding PROM1.

The present invention also provides a method for restoring vision to a subject, the method comprising introducing a vector containing an optimized sequence encoding PROM1 into the eye. The method may include subretinal or intravitreal administration of a nucleic acid vector to the inner retinal cells of the eye. The present invention provides a nucleic acid vector for use in restoring vision to a subject, the nucleic acid vector comprising an optimized sequence encoding PROM1.

The present invention also provides a method of treating a retinal disease in a subject, the method comprising introducing a vector containing an optimized sequence encoding PROM1 into the eye. The method may include subretinal or intravitreal administration of a nucleic acid vector to the inner retinal cells of the eye. The disease can be retinal dystrophy, including rod dystrophy, rod cone dystrophy, cone rod dystrophy, cone dystrophy and macular dystrophy; other forms of retinal or macular degeneration, ischemic conditions, retina pigmentosis, uveitis, and any other diseases caused by the loss of the ability of photoreceptor cells.

As used herein, providing a photoreceptor cell function to a cell means that a cell that previously did not have photoreceptor cell capacity or whose photoreceptor cell capacity has been completely or partially degraded becomes photoreceptor after expressing a foreign nucleic acid sequence encoding PROM1 therein. Such cells may be referred to herein as transformed cells because they contain unnatural nucleic acids therein. Preferably, the transformed retinal cells exhibit some or all of the photoreceptor capabilities of the natural photoreceptor cells. Preferably, the transformed cells exhibit at least the same or substantially the same photosensitivity of natural retinal photoreceptor cells. Preferably, the transformed cells exhibit higher photosensitivity than natural retinal photoreceptor cells that are diseased or degenerating. Therefore, transformed cells will preferably have increased photoreceptor cells compared to untreated degraded or diseased cells from the same source, maintained under the same conditions. Transformed cells can be distinguished from natural cells by the presence of exogenous nucleic acids.

As used herein, expanding the photoreceptor cell function means increasing the photoreceptor cell function of the retina by increasing the function in photoreceptor cells such as rods or cones and/or by providing the photoreceptor cell function to the cells. Therefore, the retina will have an increased ability to receive light signals and transmit such signals compared to a retina that has not been treated with the methods described herein, and the increase can be any amount.

As used herein, restoring vision in a subject means that the subject shows improved vision compared to before treatment, for example, using a vision test as described herein. Restoration includes any degree of improvement, including the complete restoration of vision to perfect or near-perfect vision.

As used herein, treating a disease means administering the nucleic acid or vector as described herein to ameliorate or alleviate one or more symptoms of a disease selected from the group consisting of: retinal dystrophy, including rod dystrophy, rod cone dystrophy, cone rod dystrophy, cone dystrophy, and macular dystrophy; another form of retinal or macular degeneration, retinitis pigmentosa, ischemic conditions, uveitis, and the ability of photoreceptor cells any other diseases caused by the loss of the ability of photoreceptor cells. Improvement or reduction can lead to improvements in peripheral or central vision, and/or day or night vision.

The method of the present invention includes introducing a nucleic acid sequence encoding PROM1 protein into the vitreous cavity of the eye. Preferably, the method comprises contacting the cell with a vector (preferably a virus, more preferably an adeno-associated virus) comprising the nucleic acid sequence encoding PROM1 protein. Preferably, the cells are retinal cells, preferably cone cells, rod cells, light-giving bipolar cells, light-removing bipolar cells, horizontal cells, ganglion cells and/or amacrine cells.

When the nucleic acid sequence and one or more enzymes are provided in multiple (two or more) doses, these doses can be separated by suitable time intervals, such as 30 seconds to several hours or one or more days.

Each dose may comprise an effective amount of nucleic acid sequences or viral vectors. The effective dose of the nucleic acid sequences or viral vectors can be in the range of $1\times10^9$-$1\times10^{16}$ virus per treatment regimen.

The present invention is based on targeting the optimized nucleic acid sequence encoding PROM1 to retinal cells to compensate for the degeneration of photoreceptor cells in the retina. The cells to which the nucleic acid sequences are targeted are cells of the retina, which are alive and capable of expressing foreign nucleic acid sequences. Retinal cells are cells of retinal, which are nerve or neuron cells and can become excited and transmit electrical signals. Preferably, the target retinal cells will be able to generate electrical signals and initiate signal cascade, resulting in signal transmission to the optic nerve. Preferably, the target retinal cells are cells of the inner retina. The target cells may be rod or cone cells, and/or may be non-photoreceptor cells (i.e., retinal cells in their natural form that are not responsive to light). The target retinal cells may include one or more cell types selected from the group consisting of rod cells, cone cells, light-giving bipolar cells, light-removing bipolar cells, horizontal cells, ganglion cells, Miller cells, and/or amacrine cells.

Therefore, when the target retinal cells are light-giving bipolar cells, light-removing bipolar cells, horizontal cells, ganglion cells and/or amacrine cells targeting the retina, the expression of nucleic acids encoding PROM1 can be referred to as ectopic expression. Therefore, the present invention includes within its scope a method for ectopic expression of a nucleic acid sequence encoding PROM1 in a non-photoreceptor cell. Such ectopic expression can provide photoreceptor function to cells through the expression of heterologous PROM1 protein. This is used to increase the photosensitivity of the retina where degeneration is observed.

Horizontal cells are inner retinal cells, which participate in signal processing and feedback to photoreceptor cells; bipolar cells are inner retinal cells and communicate between rod/cone cells and amacrine and/or ganglion cells; amacrine cells are found in the inner retina and allow communication between photoreceptor pathway and ganglion cells; ganglion cells are the innermost retinal cells, which transmit signals from photoreceptor cells to optic nerve.

References to cells herein include the progeny of cells. Preferably, the modification of the cell according to the present invention also occurs in subsequent generations of the transformed host cell. The progeny cells may not be consistent with the originally targeted cells, but will preferably also exhibit unnatural expression of PROM1.

Compared with the prior art, the invention mainly has the following advantages:

1. The present invention specifically optimizes the PROM1 gene sequence, which is different from the prior art. Compared with the unoptimized DNA coding sequence SEQ ID NO. 2 of PROM1 protein, the PROM1 protein expression level of the optimized sequence (SEQ ID NO: 1) and the photosensitivity of cells containing the optimized sequence were significantly improved, and the peak value of a wave of electroretinogram was stronger.

2. The optimized PROM1 protein coding sequence of the present invention is very suitable for expression in mammals. In the present invention, the expressed PROM1 protein not only maintains the activity of the natural PROM1 protein, but also has high expression amount of the PROM1 protein and strong cell photosensitivity, which can effectively treat eye diseases caused by PROM1 mutation, and has good safety.

The present invention is further described below with reference to specific embodiments. It should be understood that these examples are only for illustrating the present invention and not intended to limit the scope of the present invention. The conditions of the experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions. Unless otherwise stated, the materials and reagents used in the examples are all commercially available products.

Example 1 Sequence Optimization

In this example, the inventors optimized the coding sequence based on the amino acid sequence of the PROM1 protein (SEQ ID NO: 3) and the natural coding sequence (SEQ ID NO: 2). In particular, the present invention optimizes the sequence fragments that affect gene expression. These sequence fragments include, but are not limited to, codon usage preference, elimination of secondary structures that are not conducive to expression (such as hairpin structures), changes in GC content, CpG dinucleotide content, mRNA secondary structures, and concealed splice sites, early polyadenylation sites, internal ribosome entry and binding sites, negative CpG islands, RNA unstable regions, repeat sequences (direct repeats, inverted repeats, etc.) and restriction sites that may affect cloning. Through analysis and experimental screening, a specially optimized DNA coding sequence as shown in SEQ ID NO: 1 was finally obtained.

As shown in FIG. 1, a recombinant adeno-associated virus vector rAAV/CBA.opti-hPROM1 carrying the optimized PROM1 coding sequence was constructed, and the sequence is shown in SEQ ID NO: 4.

In addition, a recombinant adeno-associated virus vector rAAV/CBA.hPROM1 carrying an unoptimized PROM1 coding sequence (SEQ ID NO: 2) was constructed. The rAAV/CBA.hPROM1 is the same as rAAV/CBA.opti-hPROM1 except that the PROM1 protein coding sequence is different (i.e. SEQ ID NO: 1 is replaced with SEQ ID NO: 2).

Example 2

1. Experimental grouping:

Experimental group 1 was 2 weeks old PROM1 KO mice receiving rAAV/CBA.opti-hPROM1 injection, experimental group 2 was 2 weeks old PROM1 KO mice receiving rAAV/CBA.hPROM1 injection, and control group was the same age PROM1 KO mice and normal mice. The feeding environment is clean, fed with national standard feed, filtered sterile water. The temperature and humidity are constant, the light is close to natural light, the intensity is 18 lux, and the 12 h/12 h day/night cycle alternates light.

2. Injection into Subretinal Space

After full mydriasis, the mice were anesthetized. Under the special ophthalmic operating microscope, a 301/2 gauge disposable sharp needle was used to puncture the cornea within the pupil range on the medial side of the corneoscleral margin to avoid hurting iris and lens. Then use a microinjector with a 33 gauge flat needle to enter along the puncture opening, the needle bypassed the lens and reaches the vitreous body, then the needle was gradually inserted into the potential retinal lacuna between the neuroretinal layer and the retinal pigment epithelium (RPE) layer and slowly injected, with an injection volume of 1 ul. 0.1% fluorescein sodium dye (safe concentration) was added to the injection carrier suspensionto conveniently observe whether the injection is successful or not and the range of mesh loss. During the injection, 2.5% hydroxypropyl methylcellulose was dropped on the eye surface to facilitate observation of the fundus at any time. Under the operation microscope, if the local retina of the fundus is clearly visible with round bulge and green color below the omentum bulge, the injection is proved to be successful. After a certain period of time, the vesicles disappeared and the local retinal bulge flattened. If the retinal bulge and the green color below it cannot be seen during the operation, or if there were complications such as massive hemorrhage in the retina, another mouse is selected for reinjection. After the operation, 1% atropine eye ointment and tetracycline cortisone eye ointment were applied, and repeated every other day for three times to reduce inflammatory reaction and prevent infection. Eighteen months after injection, the animals were sacrificed and their eyeballs were taken for pathological examination. One eye of each mouse was injected with 1 μl rAAV/CBA.opti-hPROM1 or rAAV/CBA.hPROM1 with a titer of $1\times10^{13}$ (treated eye), and the other eye was not injected (untreated eye or uninjected eye).

3. Western Blot Detection of Protein Expression

HEK-293 cells were infected with rAAV/CBA.opti-hPROM1 and rAAV/CBA.hPROM1, respectively, and untransfected HEK-293 cells were used as controls. Two days after infection, the protein was extracted, and the protein expression was detected by Western blot, and the relative expression of PROM1 protein was detected.

The results were detected by standard Western blot assay. The protein samples were treated with protein extraction kit (Tiangen) and human PROM1 primary antibody (1:1000 dilution).

Figure 2:
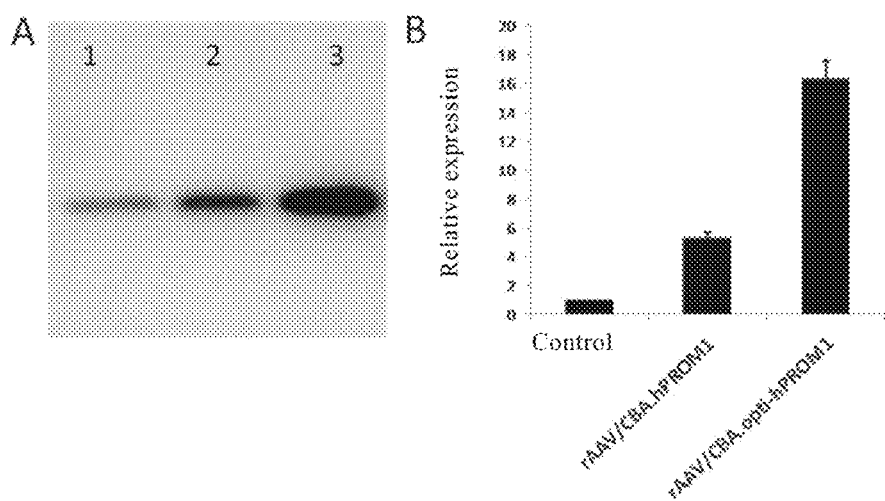
FIG. 2 shows that the sequence optimized opti-hPROM1 has a higher expression efficiency than the original hPROM1. Figure A is the results of Western blot protein electrophoresis, lane 1: control HEK-293 cells; lane 2: HEK-293 cells transfected with rAAV/CBA.hPROM1; Lane 3: HEK-293 cells transfected with rAAV/CBA.opti-hPROM1. Figure B is the relative expression level of optimized rAAV/CBA.opti-hPROM1 to rAAV/CBA.hPROM1, and figure B is the quantification of the signal strength in figure A, with lane 1 signal set to 1, and lane 2 and lane 3 taking 1 as a reference comparison value.

The results are shown in FIG. 2. The expression level of opti-hPROM1 was significantly higher than that of the unoptimized hPROM1, and the expression level was about 3.2 times that of the unoptimized hPROM1 sequence.

4. Detection of Visual Electrophysiology

Reti. Port system (Roland Company, Germany) was used, and the stimulator was Ganzfeld Q450SC UV full-field spherical stimulator. The recording electrode was a gold foil ring corneal electrode with a diameter of 3 rain; both the reference electrode and the ground electrode were stainless steel needle electrodes, the impedance of each electrode was less than 5 Q, and the interference amplitude was less than 20 pV. Both eyes were simultaneously recorded with electroretinogram (Full. field electroretinograms. F-ERGs), the recording time was consistent to reduce the difference caused by circadian rhythm, and the time of recording all selected between 14:00 and 17:00 every day. Before F. ERGs recording, the mice were dark-adapted overnight. During the experiment, 10% chloral hydrate was injected into the abdominal cavity of the mice for anesthesia, and the pupils were dilated with compound tropicamide eye drops. When the muscles of the whole body of the mouse were relaxed, the eyes were gently wiped with cotton swabs stained with normal saline to make the eyeball exophthalmos, and then placed on a 37° C. constant temperature water bath table. Electrodes were inserted under dark red light, recording electrodes were placed on the left and right corneas respectively, and a drop of 1% sodium carboxymethyl cellulose eye drops was dropped locally to keep the cornea moist and increase conductivity: the reference electrode inserted subcutaneously in the middle of the forehead, and the grounding electrode was placed at the tail. After dark adaptation for 5 min, the dark adaptation ERG (Scotopic electroretinogram, Scot-ERG) and the bright adaptation ERG (Photopic electroretinogram, Phot. ERG) were recorded sequentially. When recording Scot. ERG, the light intensity was 2.0 log cd-s/m$^2$; when recording Phot.ERG, the first bright adaptation was 10 minutes, and the stimulation light intensity was 1.08 log cd-s/m$^2$.

PROM1 KO mice received subretinal injection of rAAV/CBA.opti-hPROM1 vector, rAAV/CBA.hPROM1 vector 14 days after birth, and the control group consisted of uninjected PROM1 KO mice and normal mice. ERG examination was performed 2 weeks after injection.

Figure 3:
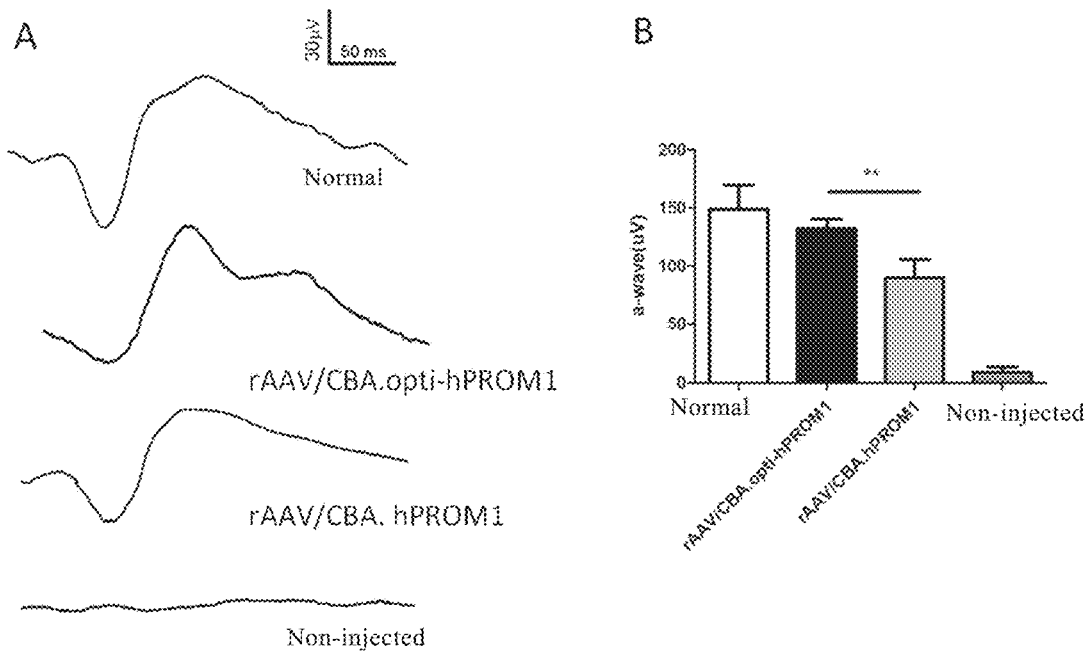
FIG. 3 shows the results of mouse electroretinogram comparison, wherein figure A shows the comparison of electroretinogram under dark adaptation of normal mice, PROM1 KO mice injected with rAAV/CBA.opti-hPROM1, PROM1 KO mice injected with rAAV/CBA.hPROM1 and PROM1 KO mice without injection from top to bottom. Figure B shows the comparison of the peak value of a wave of electroretinogram under dark adaptation of normal mice, PROM1 KO mice injected with rAAV/CBA.opti-hPROM1, PROM1 KO mice injected with rAAV/CBA.hPROM1, and PROM1 KO mice without injection. The peak value of a wave in the injected eye is much higher than that in the non-injected eye. There was no significant difference between rAAV/CBA.opti-hPROM1 and the normal control, but the therapeutic effect of rAAV/CBA.hPROM1 was not as good as that of rAAV/CBA.opti-hPROM1, and there was a significant difference ($p<0.01$).

The results are shown in FIG. 3, which shows the comparison of the peak value of a wave of electroretinogram under dark adaptation of normal mice, PROM1 KO mice injected with rAAV/CBA.opti-hPROM1, PROM1 KO mice injected with rAAV/CBA.hPROM1, and PROM1 KO mice without injection. The peak value of a wave of the injected eye was much higher than that of the uninjected eye, and the uninjected eye basically did not have any retinal rod cell function. There was no significant difference between rAAV/

CBA.opti-hPROM1 and the normal control, but the therapeutic effect of rAAV/CBA.hPROM1 was not as good as that of rAAV/CBA.opti-hPROM1, and there was a significant difference (p<0.01).

5. Immunohistochemical Detection:

(1) Preparation of frozen sections of eyeball: the mice were sacrificed by cervical dislocation method. Before the eyeballs were taken out, a pin was used to mark the apex at 12:00 above the scleral rim of the eyeball corner of the mouse. Quickly remove the eyeball with curved forceps and immediately put it in 0.01 mol/L PBS; immediately soak the eyeball in a freshly prepared 4% paraformaldehyde solution, and puncture on the cornea edge with a 16.19 gauge thick needle on 5 ml disposable syringe, overnight at 4° C. The eyeball was dehydrated with PBS solution containing sucrose with gradients of 10%, 20%, and 30%, respectively. Cut off the cornea, separate the lens, and embed the tissue with an Optimal cutting temperature compound (OCT) for 2 h, and quick-freeze with liquid nitrogen. 12-m frozen sections of eyeballs were prepared with a cryostat and placed on the attached glass slides and stored in −80° C. refrigerator.

(2) Immunofluorescence staining: The frozen sections were taken out from −80° C. refrigerator, dried in the air for 30 min, rinsed in 0.01 mol/L PBS, and washed quickly once, 5 min×2 times, 10 min×2 times. The sections were soaked in 0.3% TritionX.100 at room temperature for 30 min; blocked with 5% bovine serum albumin and soaked at room temperature for 2 h. The serum was aspirated, and rabbit anti-human PROM1 primary antibody (1:500) was added with a pipetting gun in a dark room, 30 ul for each specimen, and incubated overnight at 4° C. The specimens were washed quickly in 0.01 mol/L PBS for 1 time, 5 min×2 times, and 10 min×2 times. The goat anti-rabbit IgG.Cy3 secondary antibody dilution (1:2000), and FITC (1:100) were dropwise added in a dark room, 30 ul for each specimen, incubated in a wet box for 1 h. The specimens were quickly rinsed in 0.1 mol/L PBS for 5 times. Finally, DAPI diluent (1:500) was dropwise added, 30 ul for each specimen, incubated for 2 min, and rinsed 5 times quickly in 0.01 mol/L PBS. A little anti-fluorescence quenching solution was added with a pipetting gun, sealed with the cover glass, and nail polish was added to the four corners of the cover glass to fix it.

Figure 4:
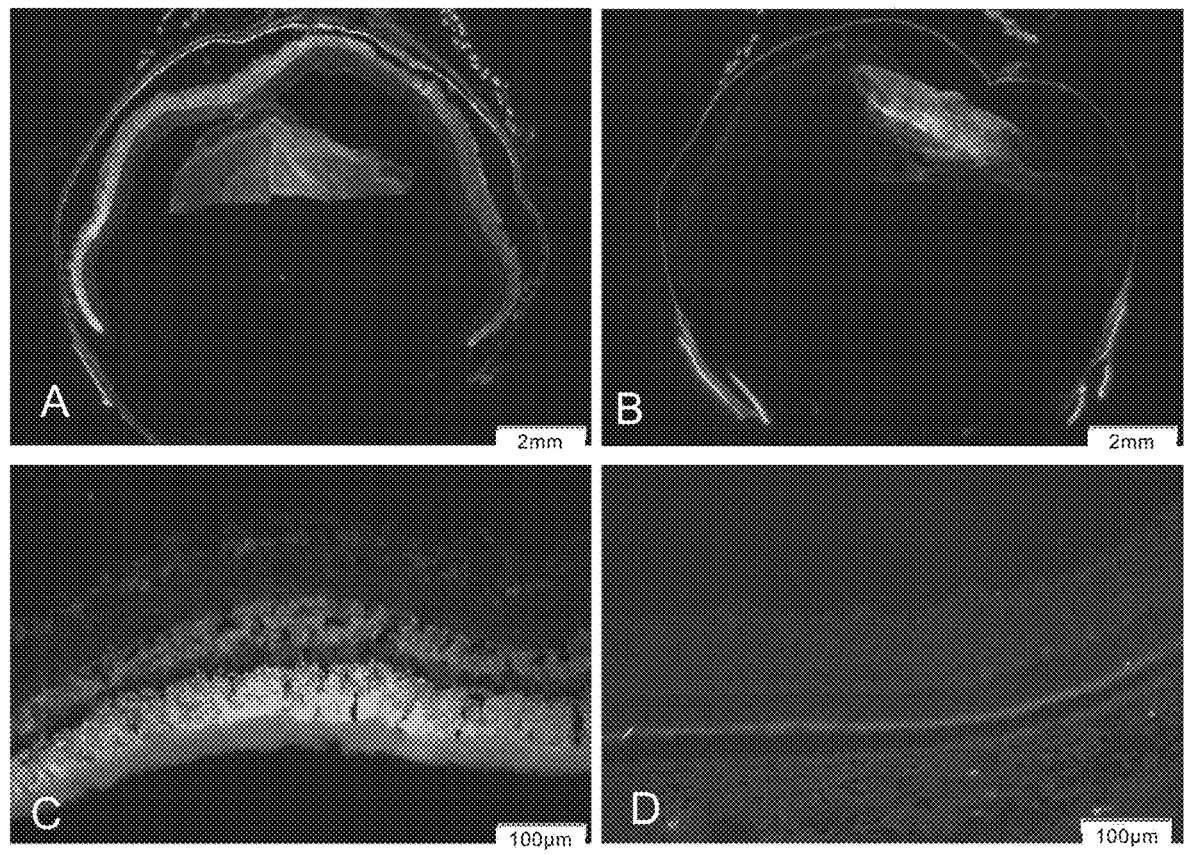
FIG. 4 shows the results of fluorescent stain of mouse retina. Wherein A: the left eye of normal C57 mice was injected with the treatment vector at the 14th day after birth, and retinal immunohistochemical detection was performed 3 weeks after injection; B: right eye without injection; scale=2 microns; C and D: detection of hPROM1 expression, scale=100 microns.
Figure 5:
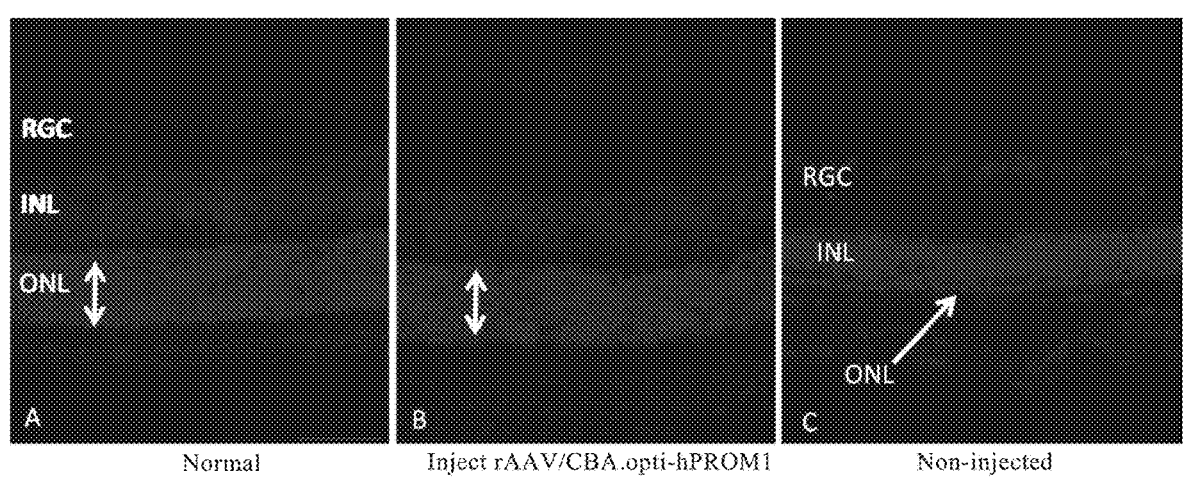
FIG. 5 shows the results of fluorescent stain of mouse retina. Figures A, B and C show DAPI staining of retinal sections of normal mice, PROM1 KO mice injected with rAAV/CBA.opti-hPROM1, and control PROM1 KO mice (non-injected), respectively. The omentum thickness of PROM1 KO mice injected with rAAV/CBA.opti-hPROM1 (Figure B) was significantly greater than that of PROM1 KO mice without injection (Figure C).

Results: (1) Detection of PROM1 expression: One eye of PROM1 KO mice was injected with rAAV/CBA.opti-hPROM1 vector in the subretinal space on the 14th day after birth, and the other eye was not injected as a control. Immunohistochemical detection of retina was performed at 3 weeks. PROM1 protein expression can be seen in the extraocular nuclear layer injected, but there is no sign of expression in the uninjected eye (FIG. 4). (2) DAPI staining: PROM1 KO mice received rAAV/CBA.opti-hPROM1 vector injection into the subretinal space in one eye on the 14th day after birth, and mice without PROM1KO injection were used as controls. Retinal immunohistochemical detection was performed at 18 months. The omentum thickness of mice injected with rAAV/CBA.opti-hPROM1 vector was significantly larger than that of mice non-injected, and there was no significant difference compared with the normal control (FIG. 5).

All documents mentioned in the present invention are cited as references in this application, as if each document is individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A nucleotide sequence, wherein the nucleotide sequence encodes a PROM1 protein, and the nucleotide sequence is selected from the group consisting of:
   (a) the nucleotide sequence of SEQ ID NO: 1; and
   (b) the nucleotide sequence having 95% or reater seguence identity to SEQ ID NO: 1; and
   (c) a nucleotide sequence complementary to the nucleotide sequence of (a) or (b).

2. An expression cassette, wherein the expression cassette comprises the nucleotide sequence of claim 1.

3. The expression cassette according to claim 2, wherein the expression cassette has a structure of formula I from the 5'-3' end:

$$Z1\text{-}Z2\text{-}Z3\text{-}Z4\text{-}Z5 \quad (I)$$

wherein, each "-" is independently a bond or nucleotide linker sequence;
Z1 is none or an enhancer,
Z2 is a promoter,
Z3 is none or an intron;
Z4 is the nucleotide sequence of claim 1; and
Z5 is none or a polyA.

4. A vector, wherein the vector comprises the nucleotide sequence of claim 1 or an expression cassette comprising the nucleotide sequence of claim 1.

5. A pharmaceutical formulation, wherein the pharmaceutical formulation comprises
   (a) the vector according to claim 4, and
   (b) a pharmaceutically acceptable carrier or excipient.

6. An adeno-associated viral vector, wherein the adeno-associated viral vector comprises the nucleotide sequence of claim 1 or an expression cassette comprising the nucleotide sequence of claim 1.

7. The adeno-associated viral vector of claim 6, wherein the sequence of the adeno-associated virus vector is the sequence of SEQ ID NO: 4.

8. A host cell, wherein the host cell comprises the vector according to claim 4.

9. The host cell of claim 8, wherein the host cell is selected from the group consisting of HEK cell, photoreceptor cell, cone cell, rod cell, bipolar cell, horizontal cell, optic nerve cell, and a combination thereof.

10. A therapeutic method comprising administering the vector of claim 4 to a subject having a retinal degenerative disease.

11. The therapeutic method according to claim 10, wherein the retinal degenerative disease is selected from the group consisting of: retinal dystrophy, retinal degeneration, macular degeneration, retinitis pigmentosa, a disease caused by loss of ability of photoreceptor cells, and a combination thereof.

12. The therapeutic method according to claim 10, wherein the retinal degenerative disease is a retinitis pigmentosa disease caused by PROM1 gene mutation.

13. The therapeutic method according to claim 10, wherein the vector is an adeno-associated viral vector.

14. A method for restoring vision or photosensitivity of a subject, which comprises:
   administering the vector of claim 4 to a subject having an eye disease.

15. The therapeutic method according to claim 14, wherein the vector is an adeno-associated viral vector.

* * * * *